(12) United States Patent
Kassab et al.

(10) Patent No.: US 11,471,182 B2
(45) Date of Patent: Oct. 18, 2022

(54) THROMBECTOMY SYSTEMS AND DEVICES AND METHODS OF USING THE SAME

(71) Applicant: CVDevices, LLC, San Diego, CA (US)

(72) Inventors: Ghassan S. Kassab, La Jolla, CA (US); Seshadri Raju, Jackson, MS (US)

(73) Assignee: CVDevices, LLC, San Diego, CA (US)

( * ) Notice: Subject to any disclaimer, the term of this patent is extended or adjusted under 35 U.S.C. 154(b) by 200 days.

(21) Appl. No.: 16/596,720

(22) Filed: Oct. 8, 2019

(65) Prior Publication Data
US 2020/0046396 A1 Feb. 13, 2020

Related U.S. Application Data

(63) Continuation of application No. 15/225,722, filed on Aug. 1, 2016, now Pat. No. 10,433,867, which is a
(Continued)

(51) Int. Cl.
*A61B 17/3207* (2006.01)
*A61B 17/22* (2006.01)
*A61F 2/95* (2013.01)

(52) U.S. Cl.
CPC .......... *A61B 17/3207* (2013.01); *A61B 17/22* (2013.01); *A61B 2017/22044* (2013.01);
(Continued)

(58) Field of Classification Search
CPC ................ A61B 17/3207; A61B 17/22; A61B 17/22031; A61B 17/22032; A61B 17/32056; A61B 17/320708; A61B 2017/22044; A61B 2017/22054; A61B 2017/22067; A61B 2017/22084; A61B 2017/320733; A61B 2017/00358; A61B 2017/22001; A61B 2017/22002; A61B 2017/22034; A61B 2017/22035;
(Continued)

(56) References Cited

U.S. PATENT DOCUMENTS 8,057,497 B1 * 11/2011 Raju ................ A61B 17/22032
606/159
2001/0049517 A1 * 12/2001 Zadno-Azizi ..... A61M 25/0071
604/509
(Continued)

*Primary Examiner* — Richard G Louis
*Assistant Examiner* — Chima U Igboko

(57) ABSTRACT

Thrombectomy systems and devices and methods of using the same. In an exemplary embodiment of a thrombectomy system of the present disclosure, the thrombectomy system comprises a thrombectomy sheath, comprising a circumferential outer wall reinforced with a reinforcement, configured as an elongated tube having a lumen therethrough; and a sonovisible element positioned at or near a distal end of the circumferential outer wall; wherein the thrombectomy sheath is sized and shaped to be at least partially positioned within a vein proximal to a thrombus or other item within the vein and further configured to expand to contact the vein to secure the thrombectomy sheath within the vein; and wherein the lumen is sized and shaped to receive a device selected from the group consisting of a balloon catheter and a snare having a loop.

20 Claims, 23 Drawing Sheets

Related U.S. Application Data continuation-in-part of application No. 13/491,754, filed on Jun. 8, 2012, now Pat. No. 10,245,049.

(60) Provisional application No. 62/199,203, filed on Jul. 30, 2015, provisional application No. 61/494,561, filed on Jun. 8, 2011.

(52) U.S. Cl.
CPC ............ *A61B 2017/22054* (2013.01); *A61B 2017/22067* (2013.01); *A61B 2017/22084* (2013.01); *A61B 2017/320733* (2013.01); *A61F 2002/9528* (2013.01)

(58) Field of Classification Search
CPC ........... A61B 2017/22051; A61B 2017/22052; A61B 2017/22055; A61B 2017/22057; A61B 2017/22058; A61B 2017/22059; A61B 2017/22061; A61B 2017/22062; A61B 2017/22064; A61B 2017/22065; A61B 2017/22068; A61B 2017/22069; A61B 2017/22071; A61B 2017/22072; A61F 2002/9528

See application file for complete search history.

(56) References Cited

U.S. PATENT DOCUMENTS

| | | | | |
|---|---|---|---|---|
| 2006/0276746 | A1* | 12/2006 | Burnside | A61M 25/10 604/103 |
| 2007/0239254 | A1* | 10/2007 | Chia | A61F 2/2436 623/1.11 |
| 2008/0077178 | A1* | 3/2008 | Janzen | A61B 17/00491 606/213 |
| 2014/0148651 | A1* | 5/2014 | Aman | A61M 29/02 600/207 |
| 2015/0173782 | A1* | 6/2015 | Garrison | A61M 25/0068 606/127 |

* cited by examiner

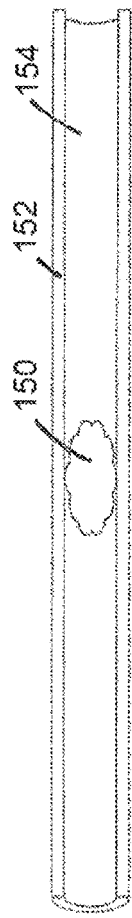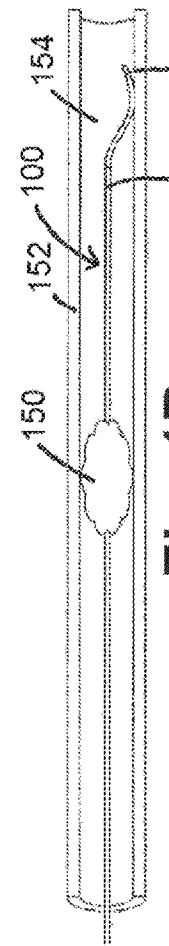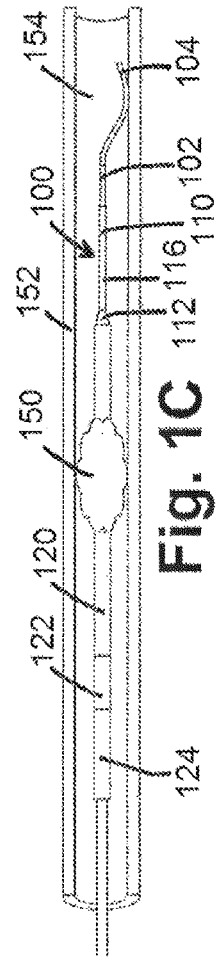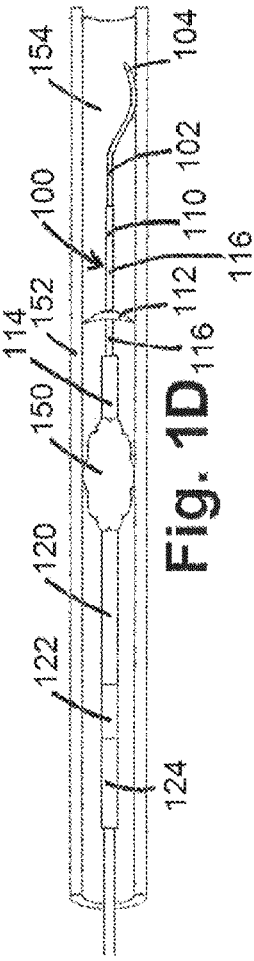

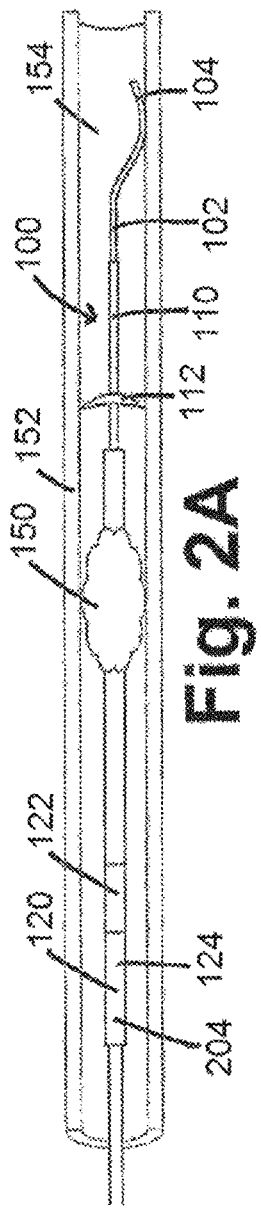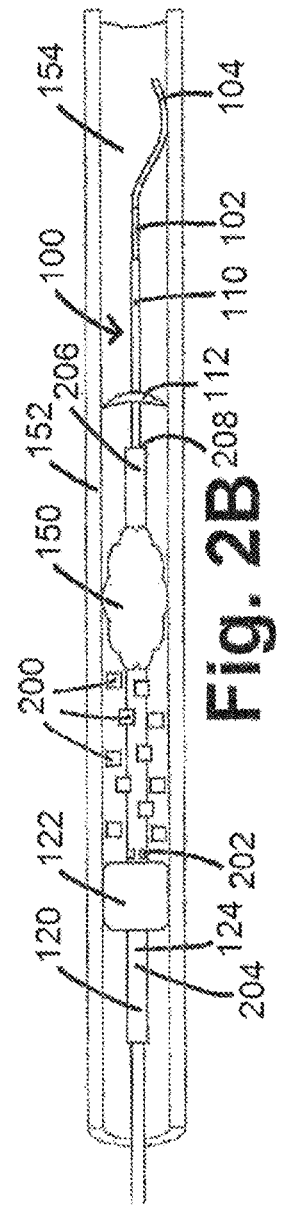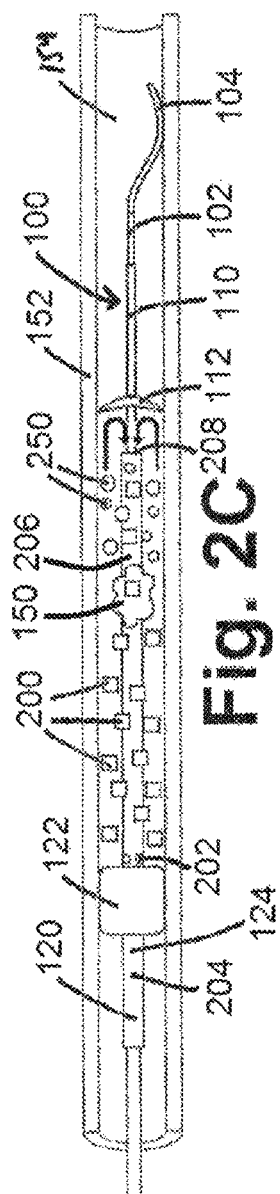

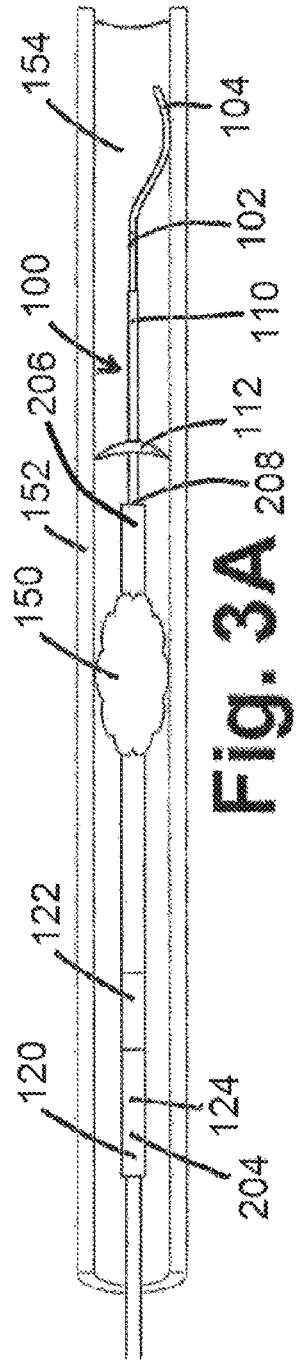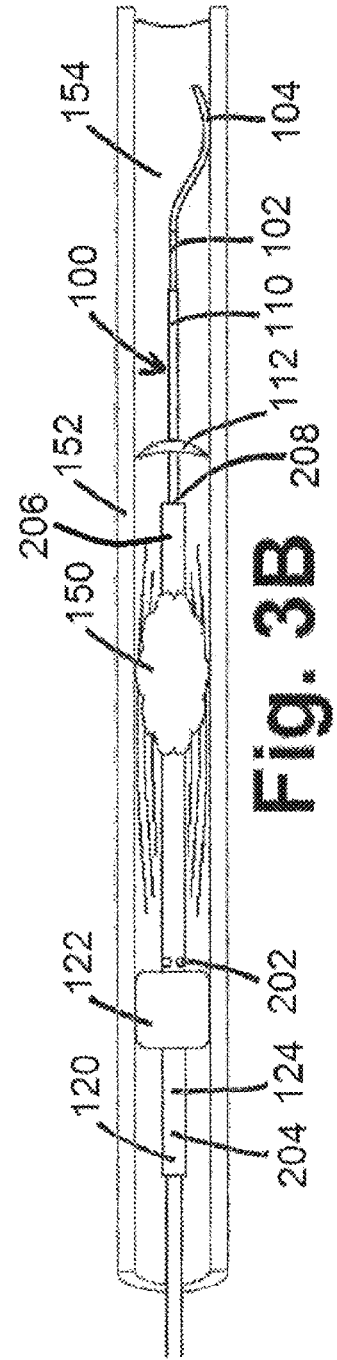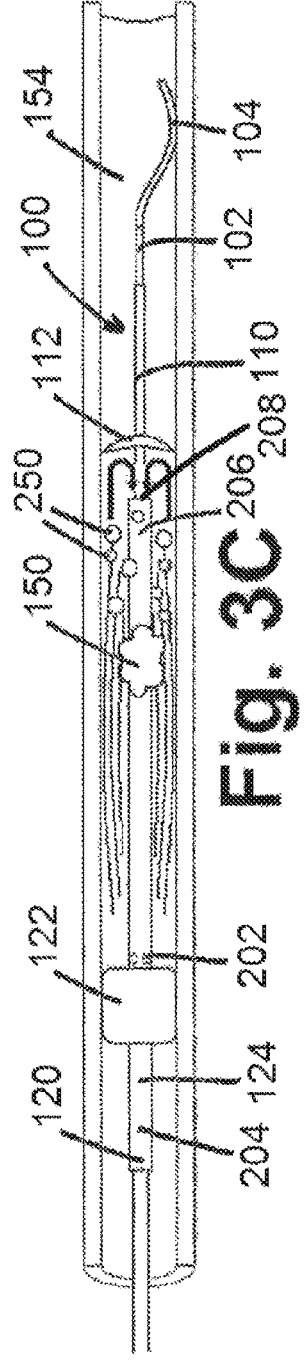

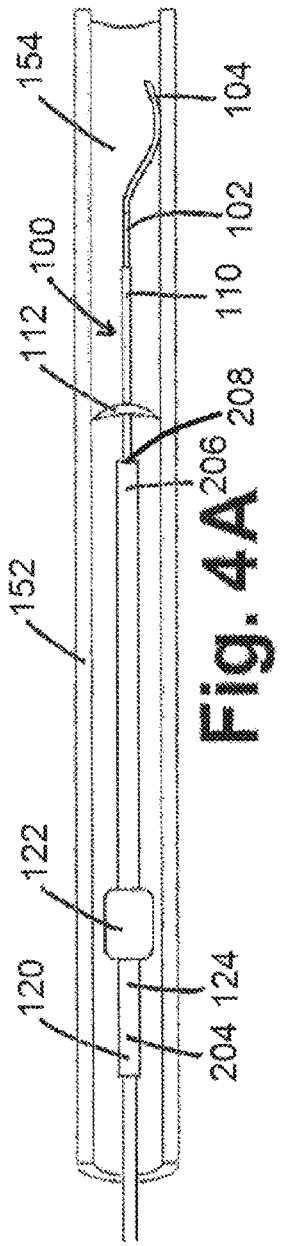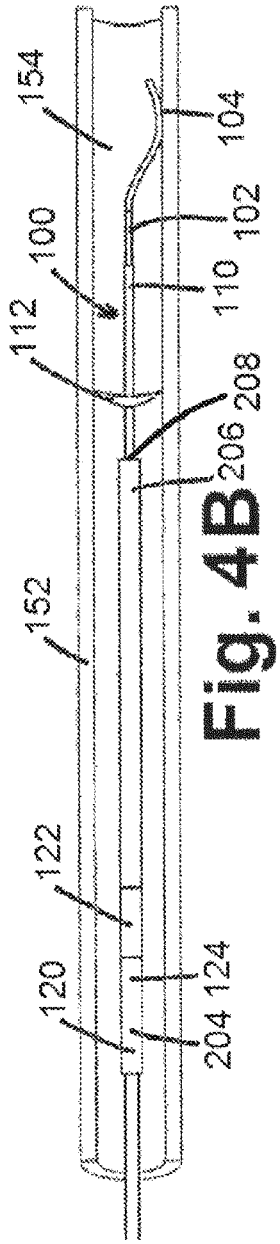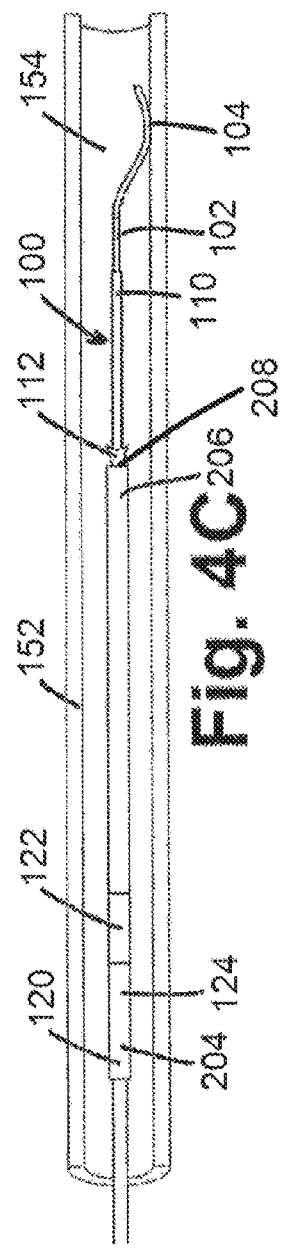

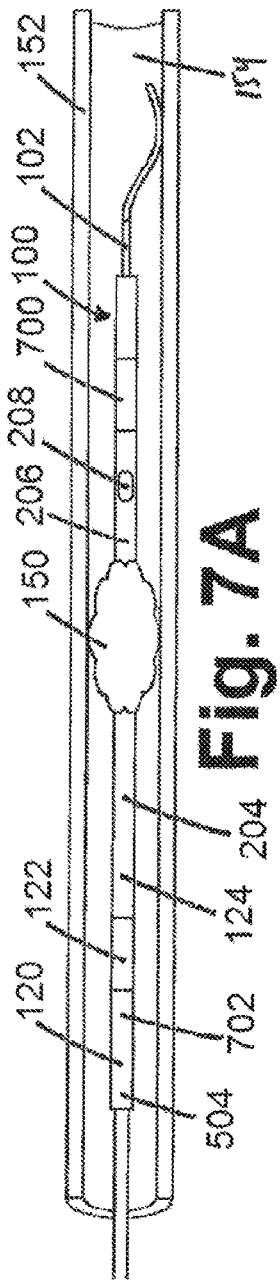 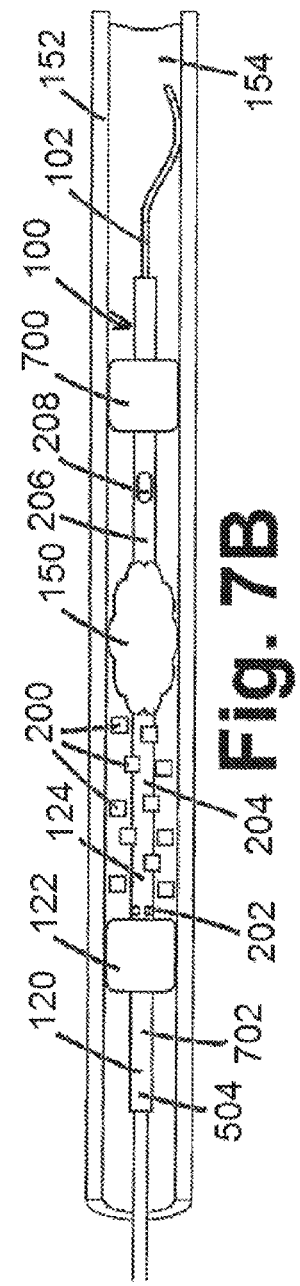 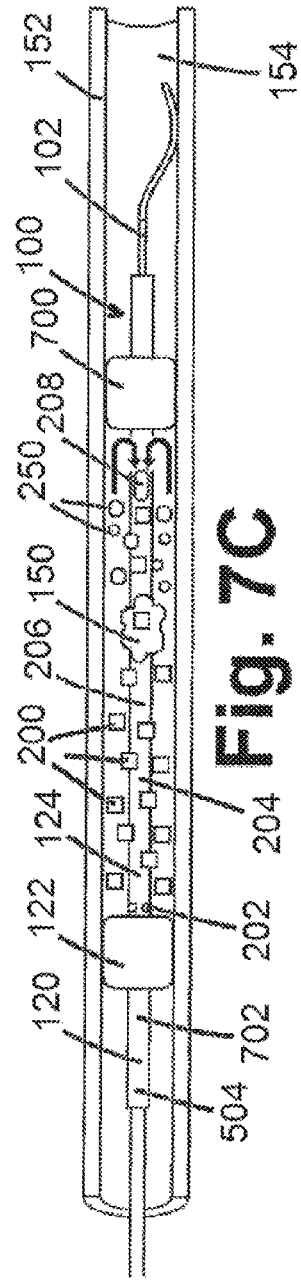

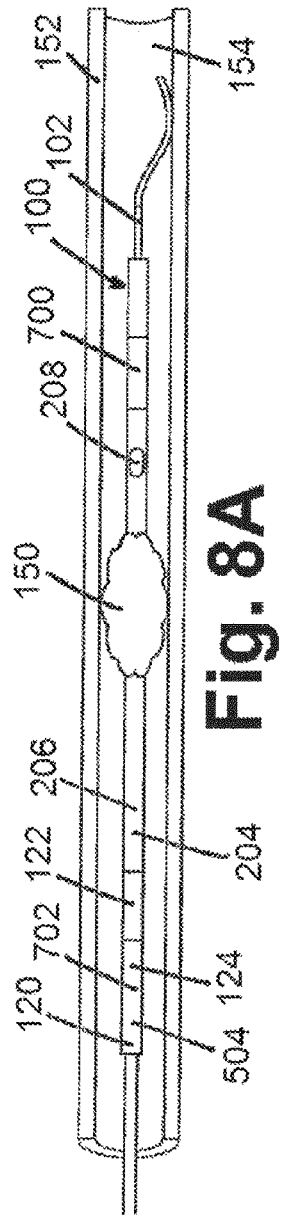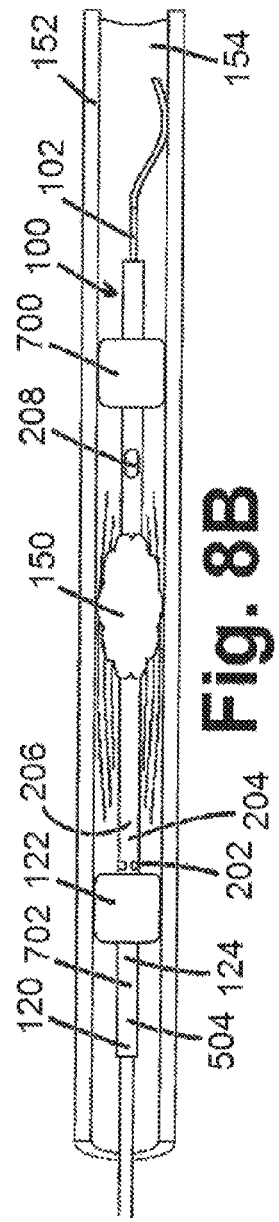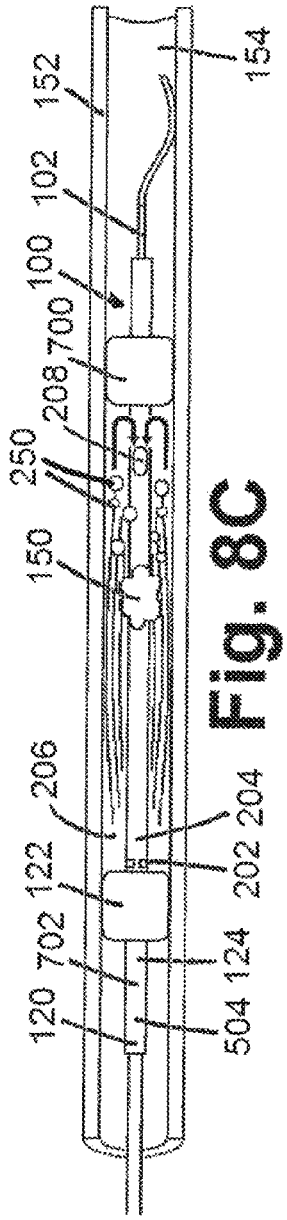

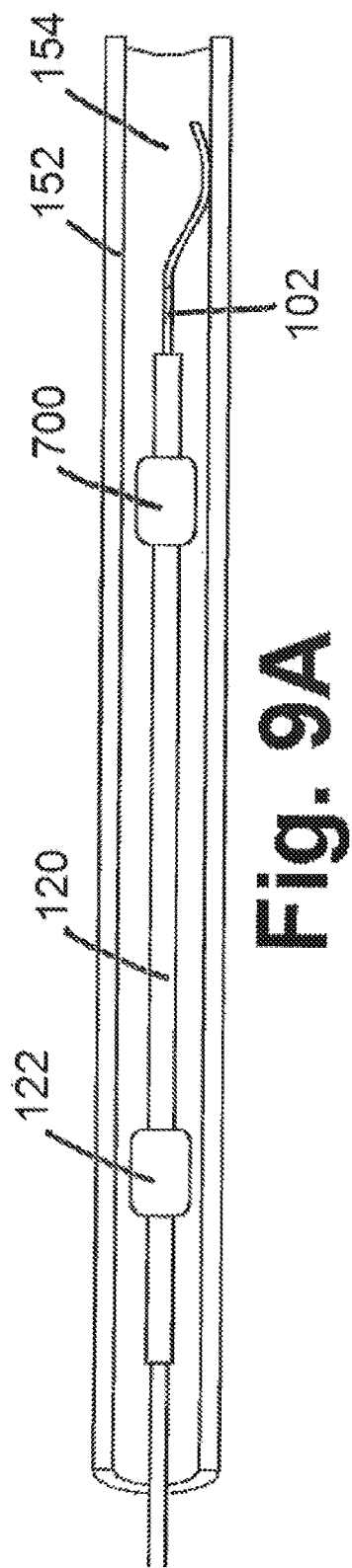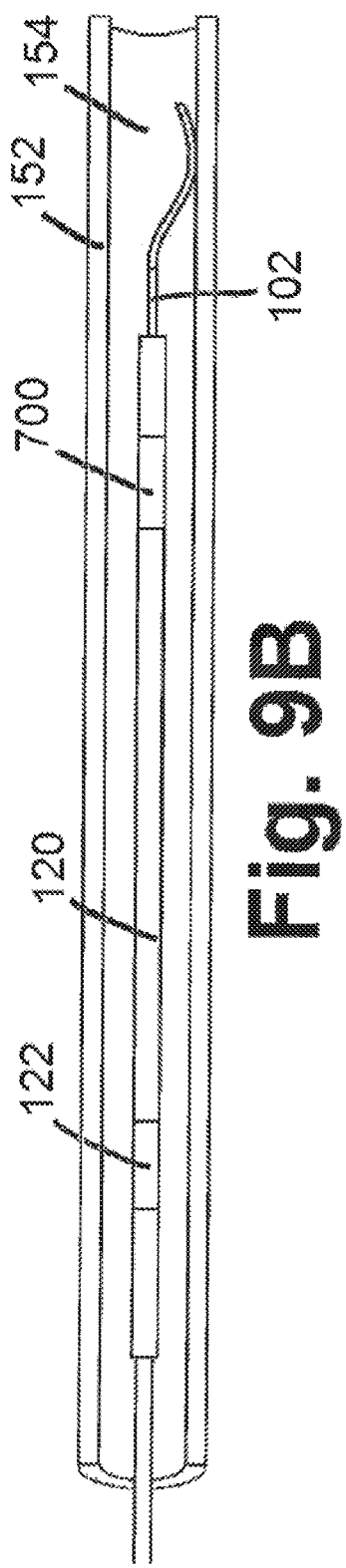

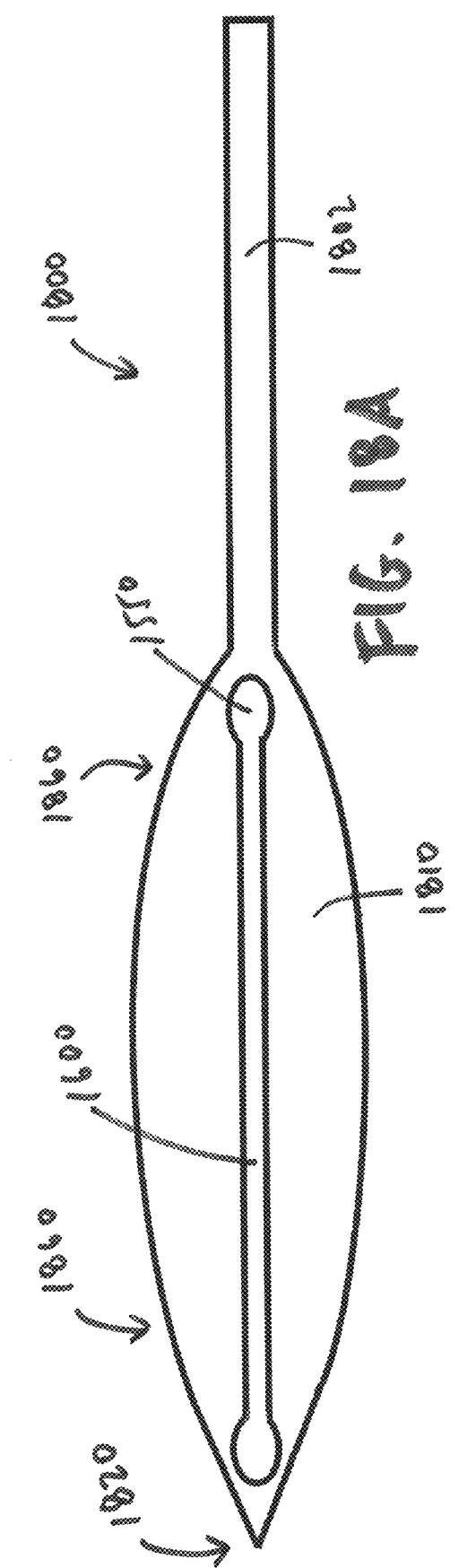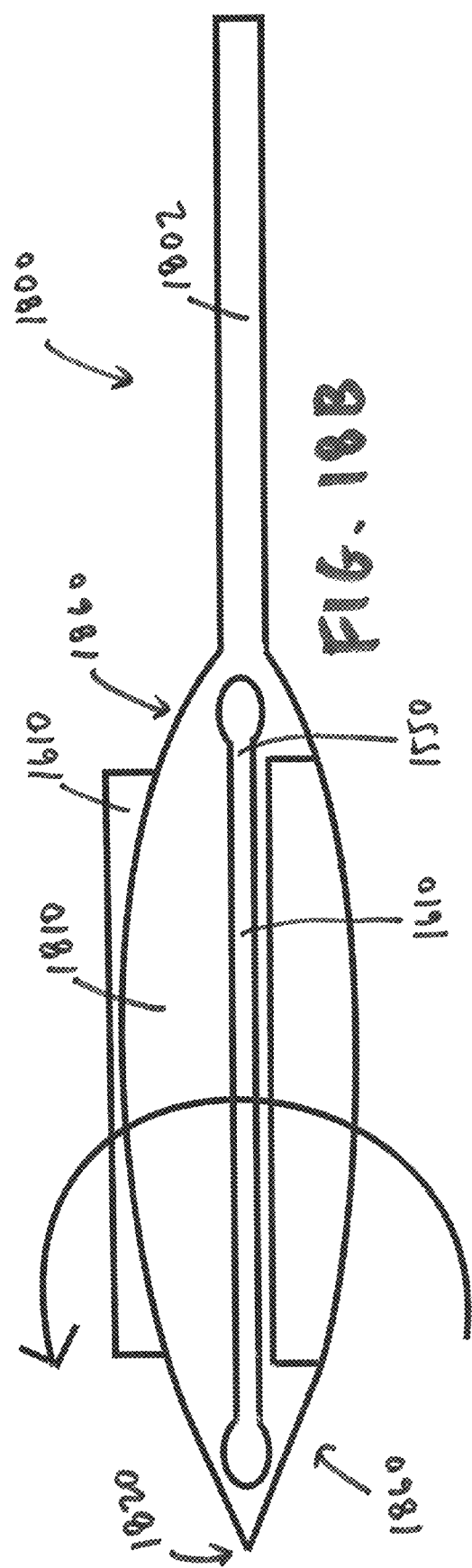

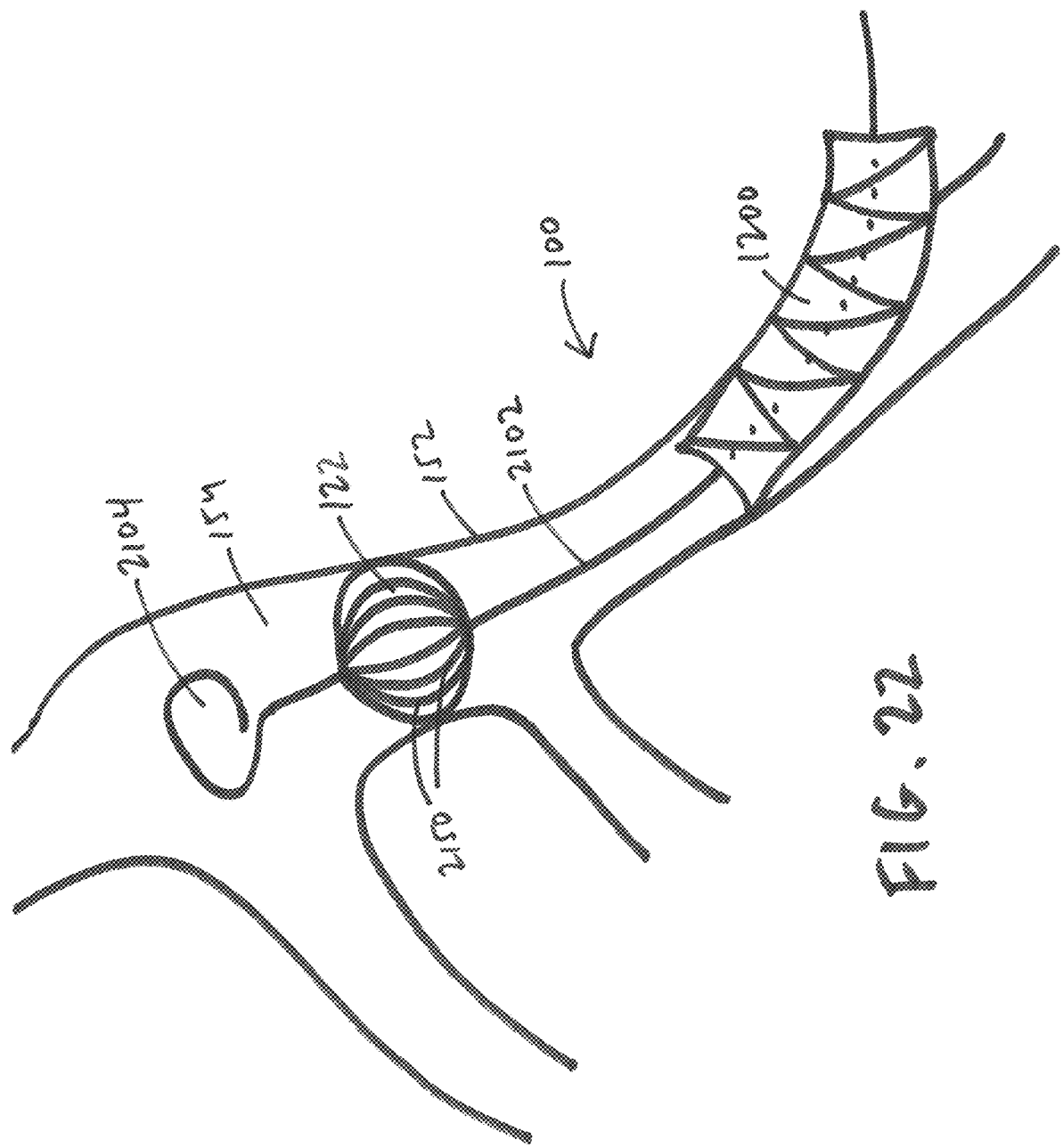

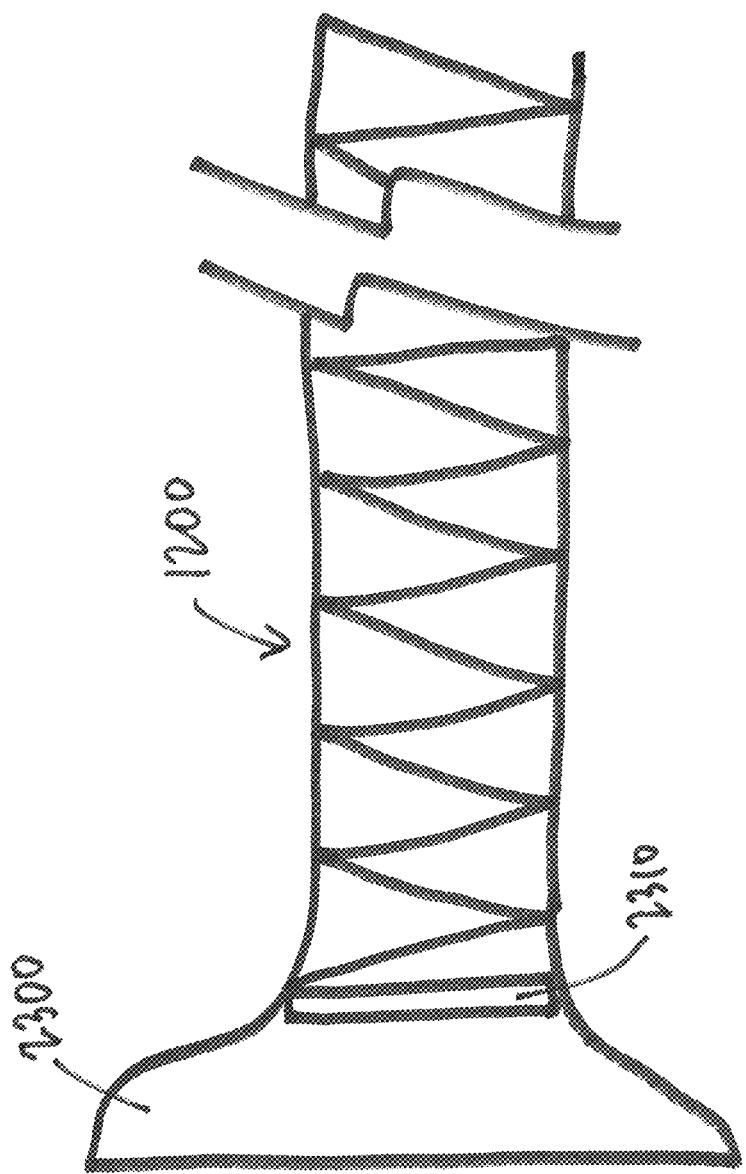

THROMBECTOMY SYSTEMS AND DEVICES AND METHODS OF USING THE SAME

PRIORITY

The present application is related to, claims the priority benefit of, and is a U.S. continuation patent application of, U.S. patent application Ser. No. 15/225,722, filed Aug. 1, 2016 and issued as U.S. Pat. No. 10,433,867 on Oct. 8, 2019, which a) is related to, and claims the priority benefit of, U.S. Provisional Patent Application Ser. No. 62/199,203, filed Jul. 30, 2015, and b) is related to, claims the priority benefit of, and is a U.S. continuation-in-part patent application of, U.S. Nonprovisional patent application Ser. No. 13/491,754, filed Jun. 8, 2012, which is related to, and claims the priority benefit of, U.S. Provisional Patent Application Ser. No. 61/494,561, filed Jun. 8, 2011. The contents of each of the aforementioned patent applications are incorporated by reference in their entirety into this disclosure.

BACKGROUND

Thrombogenesis, which involves the localized accumulation of blood elements on an injured vessel wall, can cause heart attacks and strokes. Although a thrombus is initially composed of platelets and fibrin that serve to limit bleeding, excessive thrombus growth can lead to thrombosis that obstructs blood vessels and hence can produce ischemia in vascular beds.

Current options for venous thrombectomy are limited. Of the two devices widely used currently, one has been recently withdrawn and the other (Angiojet™) is known to produce side effects such as hemoglobinuria, renal failure and pancreatitis in patients. Furthermore, the small catheter size is limiting its usefulness in extensive thrombosis; fluid overload is a concern as saline has to be injected to pulverize the clot drawn into the catheter.

In patients at risk of thrombosis, conventional drug treatments (such as aspirin, heparin, and warfarin, for example) are used to slow thrombus growth. However, such treatments have the risk of bleeding complications that can be serious and sometimes fatal. For patients that develop a thrombus, there are approaches known in the art for retrieval of the thrombus (such as catheters and balloons) as well as chemical approaches to dissolve the throbmus (such as tissue plasminogen activators or plasmin). The chemicals, however, are not localized to the throbmus and can circulate through the patient's blood and cause bleeding. Hence, there is a need for localization of thrombus dissolution either chemically or physically and its removal without affecting the rest of the cardiovascular system.

BRIEF SUMMARY

The disclosure of the present application provides various thrombus removal systems and devices and methods of using the same.

In an exemplary embodiment of a thrombus removal system of the present disclosure, the thrombus removal system comprises an umbrella catheter comprising an umbrella catheter tube and an umbrella positioned at least partially within the umbrella catheter tube when in a compressed configuration and positioned external to the umbrella catheter tube when in a deployed configuration, and a balloon catheter configured to fit around at least part of the umbrella catheter, the balloon catheter comprising a balloon catheter tube and a balloon coupled thereto, the balloon capable of inflation within a lumen of a mammalian vessel to substantially or completely occlude the lumen of the mammalian vessel, the thrombus removal system configured to disrupt and/or dissolve and remove at least a portion of a thrombus positioned within the lumen of the mammalian vessel. In another embodiment, at least part of the umbrella catheter is configured to fit around a guidewire. In yet another embodiment, the system further comprises a guidewire having a distal end, the guidewire configured to puncture the thrombus and further configured to allow at least part of the umbrella catheter to fit around the guidewire. In an additional embodiment, the umbrella is configured to at least substantially occlude the lumen of the mammalian vessel when in the deployed configuration.

In an exemplary embodiment of a thrombus removal system of the present disclosure, wherein the umbrella is configured to at allow fluid to pass therethrough but prevent at least a portion of the thrombus from passing therethrough when in the deployed configuration. In an additional embodiment, the system is configured to introduce one or more chemical agents into the lumen of the mammalian vessel, the one or more chemical agents capable of disrupting and/or dissolving at least a portion of the thrombus. In yet an additional embodiment, the one or more chemical agents are selected from the group consisting of a tissue plasminogen activator, plasmin and thrombin.

In an exemplary embodiment of a thrombus removal system of the present disclosure, the balloon catheter tube further defines one or more apertures therein, the one or more apertures configured to allow a fluid and/or a substance to pass therethrough from a first balloon catheter lumen defined within the balloon catheter tube. In another embodiment, the balloon catheter tube is configured so that one or more chemical agents can be introduced through the first balloon catheter lumen, through the one or more apertures, and into the lumen of the mammalian vessel. In another embodiment, the balloon catheter tube further defines a distal tube aperture in communication with a second balloon catheter lumen, wherein a fluid and/or a substance from within the lumen of the mammalian vessel can enter second balloon catheter lumen through the distal tube aperture when suction is applied through the second balloon catheter lumen. In an additional embodiment, the balloon catheter tube further defines a distal tube aperture in communication with a second balloon catheter lumen, wherein at least a portion of the thrombus from within the lumen of the mammalian vessel can enter second balloon catheter lumen through the distal tube aperture when suction is applied through the second balloon catheter lumen to remove at least a portion of the thrombus. In yet an additional embodiment, the balloon catheter tube is configured so that a fluid can be introduced through the first balloon catheter lumen, through the one or more apertures, and into the lumen of the mammalian vessel to flush the lumen of the mammalian vessel.

In an exemplary embodiment of a thrombus removal system of the present disclosure, the system is configured to introduce one or more disruptive oscillations into the lumen of the mammalian vessel, the one or more disruptive oscillations capable of disrupting at least a portion of the thrombus. In an additional embodiment, the one or more disruptive oscillations are introduced via ultrasound through one or more of the balloon catheter and the umbrella catheter. In yet an additional embodiment, the balloon is capable of inflation and deflation by way of an inflation/deflation lumen defined within the balloon catheter tube. In another embodiment, the system further comprises an inflation/deflation source in communication with the inflation/deflation lumen, the inflation/deflation source capable of inflating and/or deflating balloon by way of a gas and/or a liquid from the inflation/deflation source.

In an exemplary embodiment of a thrombus removal system of the present disclosure, the system further comprises a substance source in communication with a first balloon catheter lumen defined within the balloon catheter tube, the substance source capable of introducing one or more chemical agents and/or or a fluid from the substance source, through the first balloon catheter lumen, through one or more apertures defined within the balloon catheter tube, and into the lumen of the mammalian vessel. In an additional embodiment, the system further comprises a suction source in communication with a second balloon catheter lumen defined within the balloon catheter tube, the suction source capable of removing fluid and/or a particulate from the lumen of the mammalian vessel during operation of the suction source.

In an exemplary embodiment of a thrombus removal system of the present disclosure, the system comprises a guidewire having a distal end, the guidewire configured to puncture a thrombus positioned within a lumen of a mammalian vessel, an umbrella catheter configured to fit around at least part of the guidewire, the umbrella catheter comprising an umbrella catheter tube and an umbrella positioned at least partially within the umbrella catheter tube when in a compressed configuration and positioned external to the umbrella catheter tube when in a deployed configuration, a balloon catheter configured to fit around at least part of the umbrella catheter, the balloon catheter comprising a balloon catheter tube and a balloon coupled thereto, the balloon capable of inflation within a lumen of a mammalian vessel to substantially or completely occlude the lumen of the mammalian vessel, the balloon catheter defining a first lumen, a second lumen, and a third lumen therethrough, the first lumen in communication with one or more apertures defined within the balloon catheter tube, the second lumen in communication with a distal tube aperture, and the third lumen in communication with the balloon, the thrombus removal system configured to disrupt and/or dissolve and remove at least a portion of the thrombus from within the lumen of the mammalian vessel by way introducing one or more chemical agents and/or one or more disruptive oscillations into the lumen of the vessel, the one or more chemical agents and/or one or more disruptive oscillations capable of disrupting and/or dissolving at least a portion of the thrombus.

In an exemplary embodiment of a thrombus removal system of the present disclosure, the system comprises a balloon catheter optionally configured to fit around at least part of an umbrella catheter, the balloon catheter comprising a balloon catheter tube and a first balloon and a second balloon coupled thereto, the first balloon and the second balloon capable of inflation within a lumen of a mammalian vessel to substantially or completely occlude the lumen of the mammalian vessel, the thrombus removal system configured to disrupt and/or dissolve and remove at least a portion of a thrombus positioned within the lumen of the mammalian vessel. In another embodiment, at least part of the umbrella catheter is configured to fit around a guidewire. In another embodiment, the system further comprises a guidewire having a distal end, the guidewire configured to puncture the thrombus and further configured to allow at least part of the balloon catheter to fit around the guidewire.

In an exemplary embodiment of a thrombus removal system of the present disclosure, the system is configured to introduce one or more chemical agents into the lumen of the mammalian vessel, the one or more chemical agents capable of disrupting and/or dissolving at least a portion of the thrombus. In an additional embodiment, the one or more chemical agents are selected from the group consisting of a tissue plasminogen activator, plasmin and thrombin. In yet an additional embodiment, the balloon catheter tube further defines one or more apertures therein, the one or more apertures configured to allow a fluid and/or a substance to pass therethrough from a first balloon catheter lumen defined within the balloon catheter tube. In another embodiment, the balloon catheter tube is configured so that one or more chemical agents can be introduced through the first balloon catheter lumen, through the one or more apertures, and into the lumen of the mammalian vessel.

In an exemplary embodiment of a thrombus removal system of the present disclosure, the balloon catheter tube further defines a removal aperture in communication with a second balloon catheter lumen, wherein a fluid and/or a substance from within the lumen of the mammalian vessel can enter second balloon catheter lumen through the removal aperture when suction is applied through the second balloon catheter lumen. In another embodiment, the balloon catheter tube further defines a removal aperture in communication with a second balloon catheter lumen, wherein at least a portion of the thrombus from within the lumen of the mammalian vessel can enter second balloon catheter lumen through the removal aperture when suction is applied through the second balloon catheter lumen to remove at least a portion of the thrombus. In yet another embodiment, the balloon catheter tube is configured so that a fluid can be introduced through the first balloon catheter lumen, through the one or more apertures, and into the lumen of the mammalian vessel to flush the lumen of the mammalian vessel. In an additional embodiment, the system is configured to introduce one or more disruptive oscillations into the lumen of the mammalian vessel, the one or more disruptive oscillations capable of disrupting at least a portion of the thrombus. In yet an additional embodiment, the one or more disruptive oscillations are introduced via ultrasound through the balloon catheter.

In an exemplary embodiment of a thrombus removal system of the present disclosure, the first balloon and the second balloon are capable of inflation and deflation by way of at least one inflation/deflation lumen defined within the balloon catheter tube. In an additional embodiment, the system further comprises an inflation/deflation source in communication with the at least one inflation/deflation lumen, the inflation/deflation source capable of inflating and/or deflating the first balloon and the second balloon by way of a gas and/or a liquid from the inflation/deflation source. In yet an additional embodiment, the system further comprises a substance source in communication with a first balloon catheter lumen defined within the balloon catheter tube, the substance source capable of introducing one or more chemical agents and/or or a fluid from the substance source, through the first balloon catheter lumen, through one or more apertures defined within the balloon catheter tube, and into the lumen of the mammalian vessel. In another embodiment, the system further comprises a suction source in communication with a second balloon catheter lumen defined within the balloon catheter tube, the suction source capable of removing fluid and/or a particulate In an exemplary embodiment of a method of removing a thrombus from a lumen of a mammalian vessel of the present disclosure, the method comprises the steps of inserting a guidewire into a lumen of a mammalian vessel through a thrombus present therein, inserting an umbrella catheter through the thrombus around at least part of the guidewire, inserting a balloon catheter through the thrombus around at least part of the umbrella catheter, deploying an umbrella of the umbrella catheter to at least substantially occlude the lumen of the mammalian vessel distal to the thrombus or to at least substantially prevent a portion of the thrombus from passing through the umbrella, inflating a balloon of the balloon catheter to at least substantially occlude the lumen of the mammalian vessel proximal to the thrombus, operating one or more of the umbrella catheter and/or the balloon catheter to disrupt and/or dissolve the thrombus, and applying suction through the balloon catheter to remove at least part of the disrupted thrombus from the lumen of the mammalian vessel. In another embodiment, the step of operating one or more of the umbrella catheter and/or the balloon catheter comprises introducing one or more chemical agents through the balloon catheter into the lumen of the mammalian vessel to disrupt and/or dissolve the thrombus. In yet another embodiment, the step of operating one or more of the umbrella catheter and/or the balloon catheter comprises introducing one or more disruptive oscillations therethrough to disrupt the thrombus. In an additional embodiment, the method further comprises the steps of deflating the balloon and inverting the umbrella so that the umbrella can be positioned at least partially within a distal aperture of the balloon catheter, and removing the guidewire, the umbrella catheter, and the balloon catheter from the lumen of the mammalian vessel.

In an exemplary embodiment of a method of removing a thrombus from a lumen of a mammalian vessel of the present disclosure, the method comprises the steps of inserting a guidewire into a lumen of a mammalian vessel through a thrombus present therein, inserting a balloon catheter through the thrombus around at least part of the guidewire, inflating a first balloon of the balloon catheter to at least substantially occlude the lumen of the mammalian vessel proximal to the thrombus and inflating a second balloon of the balloon catheter to at least substantially occlude the lumen of the mammalian vessel distal to the thrombus, operating the balloon catheter to disrupt and/or dissolve the thrombus, and applying suction through the balloon catheter to remove at least part of the disrupted thrombus from the lumen of the mammalian vessel. In another embodiment, the step of operating the balloon catheter comprises introducing one or more chemical agents through the balloon catheter into the lumen of the mammalian vessel to disrupt and/or dissolve the thrombus. In another embodiment, the step of operating the balloon catheter comprises introducing one or more disruptive oscillations therethrough to disrupt the thrombus. In an additional embodiment, the method further comprises the steps of deflating the first balloon and the second balloon, and removing the guidewire and the balloon catheter from the lumen of the mammalian vessel.

In an exemplary embodiment of a thrombus removal system of the present disclosure, the thrombus removal system comprises a balloon catheter comprising a balloon catheter tube and a first balloon coupled thereto, the first balloon capable of inflation within a lumen of a mammalian vessel to substantially or completely occlude the lumen of the mammalian vessel, and a second occlusion element configured to at least substantially occlude the lumen of the mammalian vessel, wherein the thrombus removal system is configured to disrupt and/or dissolve and remove at least a portion of a thrombus positioned within the lumen of the mammalian vessel. In another embodiment, the second occlusion element comprises an umbrella catheter comprising an umbrella catheter tube and an umbrella positioned at least partially within the umbrella catheter tube when in a compressed configuration and positioned external to the umbrella catheter tube when in a deployed configuration, wherein the umbrella is configured to at least substantially occlude the lumen of the mammalian vessel when in the deployed configuration, and wherein the balloon catheter is configured to fit around at least part of the umbrella catheter. In yet another embodiment, the thrombus removal system further comprises a guidewire having a distal end, the guidewire configured to puncture the thrombus, wherein at least part of the umbrella catheter is configured to fit around the guidewire. In an additional embodiment, the umbrella is configured to at allow fluid to pass therethrough but prevent at least a portion of the thrombus from passing therethrough when in the deployed configuration. In an exemplary embodiment of a thrombus removal system of the present disclosure, when the first balloon is positioned proximal to the thrombus and inflated to at least substantially occlude the lumen of the mammalian vessel and wherein when the umbrella is positioned distal to the thrombus and operated to at least substantially occlude the lumen of the mammalian vessel, operation of one or more of the umbrella catheter and/or the balloon catheter can disrupt and/or dissolve the thrombus, and use of suction through the balloon catheter can facilitate removal of at least part of the disrupted thrombus from the lumen of the mammalian vessel. In an additional embodiment, the first balloon is capable of inflation and deflation by way of an inflation/deflation lumen defined within the balloon catheter tube.

In an exemplary embodiment of a thrombus removal system of the present disclosure, the second occlusion element comprises a second balloon coupled to the balloon catheter tube, the second balloon capable of inflation within the lumen of the mammalian vessel to substantially or completely occlude the lumen of the mammalian vessel, and wherein the first balloon and the second balloon are capable of inflation and deflation by way of at least one inflation/deflation lumen defined within the balloon catheter tube. In another embodiment, when the first balloon is positioned proximal to the thrombus and inflated to at least substantially occlude the lumen of the mammalian vessel and wherein when the second balloon is positioned distal to the thrombus and inflated to at least substantially occlude the lumen of the mammalian vessel, operation of the balloon catheter can disrupt and/or dissolve the thrombus, and use of suction through the balloon catheter can facilitate removal of at least part of the disrupted thrombus from the lumen of the mammalian vessel. In yet another embodiment, the system is configured to introduce one or more chemical agents into the lumen of the mammalian vessel, the one or more chemical agents capable of disrupting and/or dissolving at least a portion of the thrombus. In an additional embodiment, the balloon catheter tube further defines one or more apertures therein, the one or more apertures configured to allow a fluid and/or a substance to pass therethrough from a first balloon catheter lumen defined within the balloon catheter tube. In yet an additional embodiment, the balloon catheter tube further defines a distal tube aperture in communication with a second balloon catheter lumen, wherein at least a portion of the thrombus from within the lumen of the mammalian vessel can enter second balloon catheter lumen through the distal tube aperture when suction is applied through the second balloon catheter lumen to remove at least a portion of the thrombus.

In an exemplary embodiment of a thrombus removal system of the present disclosure, the balloon catheter tube is configured so that a fluid can be introduced through the first balloon catheter lumen, through the one or more apertures, and into the lumen of the mammalian vessel to flush the lumen of the mammalian vessel. In an additional embodiment, the system is configured to introduce one or more disruptive oscillations through one or more of the balloon catheter and a portion of the second occlusion element and into the lumen of the mammalian vessel, wherein the one or more disruptive oscillations capable of disrupting at least a portion of the thrombus. In yet an additional embodiment, the thrombus removal system further comprises a substance source in communication with a first balloon catheter lumen defined within the balloon catheter tube, the substance source capable of introducing one or more chemical agents and/or or a fluid from the substance source, through the first balloon catheter lumen, through one or more apertures defined within the balloon catheter tube, and into the lumen of the mammalian vessel. In another embodiment, the thrombus removal system further comprises a suction source in communication with a second balloon catheter lumen defined within the balloon catheter tube, the suction source capable of removing fluid and/or a particulate from the lumen of the mammalian vessel during operation of the suction source.

In an exemplary embodiment of a thrombus removal system of the present disclosure, the thrombus removal system comprises a guidewire having a distal end, the guidewire configured to puncture a thrombus positioned within a lumen of a mammalian vessel, a balloon catheter comprising a balloon catheter tube and a first balloon coupled thereto, the first balloon capable of inflation within a lumen of a mammalian vessel to substantially or completely occlude the lumen of the mammalian vessel, and a second occlusion element configured to at least substantially occlude the lumen of the mammalian vessel, the second occlusion element selected from the group consisting of (i) an umbrella catheter comprising an umbrella catheter tube and an umbrella positioned at least partially within the umbrella catheter tube when in a compressed configuration and positioned external to the umbrella catheter tube when in a deployed configuration, wherein the umbrella is configured to at least substantially occlude the lumen of the mammalian vessel when in the deployed configuration, and (ii) a second balloon coupled to the balloon catheter tube, the second balloon capable of inflation within the lumen of the mammalian vessel to substantially or completely occlude the lumen of the mammalian vessel, the thrombus removal system configured to disrupt and/or dissolve and remove at least a portion of the thrombus from within the lumen of the mammalian vessel by way introducing one or more chemical agents and/or one or more disruptive oscillations into the lumen of the vessel, the one or more chemical agents and/or one or more disruptive oscillations capable of disrupting and/or dissolving at least a portion of the thrombus.

In an exemplary embodiment of a thrombectomy system of the present disclosure, the thrombectomy system comprises a thrombectomy sheath, comprising a circumferential outer wall reinforced with a reinforcement, configured as an elongated tube having a lumen therethrough; and a sonovisible element positioned at or near a distal end of the circumferential outer wall; wherein the thrombectomy sheath is sized and shaped to be at least partially positioned within a vein proximal to a thrombus or other item within the vein and further configured to expand to contact the vein to secure the thrombectomy sheath within the vein; and wherein the lumen is sized and shaped to receive a device selected from the group consisting of a balloon catheter and a snare having a loop.

In an exemplary embodiment of a thrombectomy system of the present disclosure, the circumferential outer wall comprises a flexible polymer material, and wherein the reinforcement comprises a metallic material.

In an exemplary embodiment of a thrombectomy system of the present disclosure, the circumferential outer wall is configured for autoexpansion.

In an exemplary embodiment of a thrombectomy system of the present disclosure, the thrombectomy system further comprises a balloon positioned at or near a distal end of the circumferential outer wall, at least partially positioned within an indention defined within the circumferential outer wall.

In an exemplary embodiment of a thrombectomy system of the present disclosure, the thrombectomy system further comprises a first obturator configured to fit within the lumen of the thrombectomy sheath, the first obturator comprising a flange configured to engage a proximal coupler of the thrombectomy sheath and defining a tapered portion at a distal end, the tapered portion configured to extend from the distal end of the thrombectomy sheath so to dilate the vein when advanced therein.

In an exemplary embodiment of a thrombectomy system of the present disclosure, the thrombectomy system further comprises a second obturator comprising an elongated portion and a cylindrical portion having a larger diameter than the elongated portion, the cylindrical portion having a hemi-cylindrical groove defined therein configured to receive at least part of the balloon catheter, and further comprising a fitting ring configured to fit upon the cylindrical portion and rotate thereon so to lock at least part of the balloon catheter within the cylindrical groove.

In an exemplary embodiment of a thrombectomy system of the present disclosure, the thrombectomy system further comprises a third obturator comprising a generally uniform cylinder having a flat tip, the third obturator configured to extend at least 2 cm from the distal end of the thrombectomy sheath when positioned therein.

In an exemplary embodiment of a thrombectomy system of the present disclosure, the thrombectomy system further comprises an ancillary dilator comprising an elongated portion and a relatively larger ovular portion having a pointed tip and defining a groove therein configured to receive at least part of a balloon catheter therein, and further comprising a fitting ring configured to fit upon the relatively larger ovular portion and rotate thereon so to lock at least part of the balloon catheter within the groove.

In an exemplary embodiment of a thrombectomy system of the present disclosure, the thrombectomy system further comprises the balloon catheter.

In an exemplary embodiment of a thrombectomy system of the present disclosure, the thrombectomy system further comprises a hemostatic plug configured to be pushed through the lumen of the thrombectomy sheath using the flat tip of the third obturator so that the hemostatic plug is positioned within the vein after being pushed out of the thrombectomy sheath.

In an exemplary embodiment of a thrombectomy system of the present disclosure, the thrombectomy system further comprises the snare having a loop, the snare configured to fit within the lumen of the thrombectomy sheath and to engage a thrombus within the vein using the loop.

In an exemplary embodiment of a thrombectomy system of the present disclosure, when the thrombectomy sheath is at least partially positioned within the vein proximal to the thrombus, the balloon catheter can be positioned through the lumen of the thrombectomy sheath so that a balloon of the balloon catheter is positioned distal to the thrombus, and whereby inflation of the balloon and retraction of the balloon catheter through the thrombectomy sheath removes the thrombus from the vein.

In an exemplary embodiment of a thrombectomy system of the present disclosure, when a guidewire is positioned within the vein and when the first obturator is positioned within the lumen of the thrombectomy sheath, advancement of the first obturator and the thrombectomy sheath within the vein along the guidewire causes the vein to dilate.

In an exemplary embodiment of a thrombectomy system of the present disclosure, the thrombectomy system comprises a thrombectomy sheath, comprising a circumferential outer wall comprising a flexible polymer material reinforced with a reinforcement comprising a metallic material, configured as an elongated tube having a lumen therethrough; and a sonovisible element positioned at or near a distal end of the circumferential outer wall; wherein the thrombectomy sheath is sized and shaped to be at least partially positioned within a vein proximal to a thrombus or other item within the vein and further configured to expand to contact the vein to secure the thrombectomy sheath within the vein; and wherein the lumen is sized and shaped to receive a device selected from the group consisting of a balloon catheter and a snare having a loop; and a first obturator configured to fit within the lumen of the thrombectomy sheath, the first obturator comprising a flange configured to engage a proximal coupler of the thrombectomy sheath and defining a tapered portion at a distal end, the tapered portion configured to extend from the distal end of the thrombectomy sheath so to dilate the vein when advanced therein.

In an exemplary embodiment of a thrombectomy system of the present disclosure, the thrombectomy system further comprises a second obturator comprising an elongated portion and a cylindrical portion having a larger diameter than the elongated portion, the cylindrical portion having a hemicylindrical groove defined therein configured to receive at least part of the balloon catheter, and further comprising a fitting ring configured to fit upon the cylindrical portion and rotate thereon so to lock at least part of the balloon catheter within the cylindrical groove.

In an exemplary embodiment of a thrombectomy system of the present disclosure, the thrombectomy system further comprises an ancillary dilator comprising an elongated portion and a relatively larger ovular portion having a pointed tip and defining a groove therein configured to receive at least part of a balloon catheter therein, and further comprising a fitting ring configured to fit upon the relatively larger ovular portion and rotate thereon so to lock at least part of the balloon catheter within the groove.

In an exemplary embodiment of a thrombectomy method of the present disclosure, the thrombectomy method comprises the steps of positioning a distal end of a thrombectomy sheath over a guidewire positioned within a vein, the thrombectomy sheath comprising a circumferential outer wall reinforced with a reinforcement, configured as an elongated tube having a lumen therethrough, and a sonovisible element positioned at or near the distal end of the circumferential outer wall, wherein the thrombectomy sheath is sized and shaped to be at least partially positioned within a vein proximal to a thrombus or other item within the vein and further configured to expand to contact the vein to secure the thrombectomy sheath within the vein, and wherein the lumen is sized and shaped to receive a device selected from the group consisting of a balloon catheter and a snare having a loop; advancing the thrombectomy sheath having a first obturator positioned therein along the guidewire so to dilate the vein at the thrombectomy sheath; and advancing the device through the lumen of the thrombectomy sheath so that a distal element of the device is positioned distal to the thrombus.

In an exemplary embodiment of a thrombectomy method of the present disclosure, the device comprises the balloon catheter, and wherein the step of advancing the device is performed to advance the balloon catheter through the lumen of the thrombectomy sheath so that a balloon of the balloon catheter is positioned distal to the thrombus; and the method further comprises the steps of inflating the balloon within the vein distal to the thrombus; and retracting the balloon catheter through the thrombectomy sheath to remove the thrombus from the vein.

In an exemplary embodiment of a thrombectomy method of the present disclosure, the device comprises the snare having the loop, and wherein the step of advancing the device is performed to advance the balloon catheter through the lumen of the thrombectomy sheath so that the loop of the snare is positioned distal to the thrombus; and the method further comprises the step of retracting the snare through the thrombectomy sheath to remove the thrombus from the vein.

In an exemplary embodiment of a thrombectomy method of the present disclosure, the method further comprises the step of positioning a filter distal to the thrombus within the vein, the filter configured to filter blood within the vein.

BRIEF DESCRIPTION OF THE DRAWINGS

The above mentioned embodiments and other features, advantages and disclosures contained herein, and the manner of attaining them, will become apparent and the present disclosure will be better understood by reference to the following description of various exemplary embodiments of the present disclosure taken in conjunction with the accompanying drawings, wherein:

FIG. 1A shows a mammalian vessel with a thrombus positioned therein, according to an embodiment of the present disclosure;

FIG. 1B shows at a guidewire positioned within a thrombus within a mammalian vessel, according to an embodiment of the present disclosure;

FIG. 1C shows an umbrella catheter and a balloon catheter positioned within a thrombus within a mammalian vessel, according to an embodiment of the present disclosure;

FIGS. 1D and 2A show a deployed umbrella of the umbrella catheter shown in FIG. 1C, according to an embodiment of the present disclosure;

FIG. 2B shows the use of a chemical agent by way of a thrombus removal system within a mammalian vessel, according to an embodiment of the present disclosure;

FIG. 2C shows the disruption and/or dissolution of at least part of a thrombus from the use of a chemical agent by way of a thrombus removal system within a mammalian vessel, according to an embodiment of the present disclosure;

FIG. 3A shows a deployed umbrella of the umbrella catheter shown in FIG. 1C, according to an embodiment of the present disclosure;

FIG. 3B shows the use of disruptive oscillations by way of a thrombus removal system within a mammalian vessel, according to an embodiment of the present disclosure;

FIG. 3C shows the disruption of at least part of a thrombus from the use of disruptive oscillations by way of a thrombus removal system within a mammalian vessel, according to an embodiment of the present disclosure;

FIG. 4A shows portions of an exemplary thrombus removal system positioned within a mammalian vessel with a partially deflated balloon, according to an embodiment of the present disclosure;

FIG. 4B shows portions of an exemplary thrombus removal system positioned within a mammalian vessel with an inverted umbrella, according to an embodiment of the present disclosure;

FIG. 4C shows portions of an exemplary thrombus removal system positioned within a mammalian vessel with some or all of the umbrella positioned within the balloon catheter, according to an embodiment of the present disclosure;

FIG. 7A shows a balloon catheter having two balloons positioned within a thrombus within a mammalian vessel, according to an embodiment of the present disclosure;

FIG. 7B shows the use of a chemical agent by way of a thrombus removal system within a mammalian vessel, according to an embodiment of the present disclosure;

FIG. 7C shows the disruption and/or dissolution of at least part of a thrombus from the use of a chemical agent by way of a thrombus removal system within a mammalian vessel, according to an embodiment of the present disclosure;

FIG. 8A shows a balloon catheter having two balloons positioned within a thrombus within a mammalian vessel, according to an embodiment of the present disclosure;

FIG. 8B shows the use of disruptive oscillations by way of a thrombus removal system within a mammalian vessel, according to an embodiment of the present disclosure;

FIG. 8C shows the disruption of at least part of a thrombus from the use of disruptive oscillations by way of a thrombus removal system within a mammalian vessel, according to an embodiment of the present disclosure;

FIG. 9A shows portions of an exemplary thrombus removal system positioned within a mammalian vessel with partially deflated balloons, according to an embodiment of the present disclosure;

FIG. 9B shows portions of an exemplary thrombus removal system positioned within a mammalian vessel with fully deflated balloons, according to an embodiment of the present disclosure;

FIG. 18A and FIG. 18B show side views of ancillary dilators, according to embodiments of the present disclosure;

FIG. 22 shows portions of a system used to retrieve a detached balloon, according to an embodiment of the present disclosure; and FIG. 23 shows a side perspective view of a thrombectomy sheath, according to an embodiment of the present disclosure.

Like reference numerals indicate the same or similar parts throughout the several figures.

Figure 5:
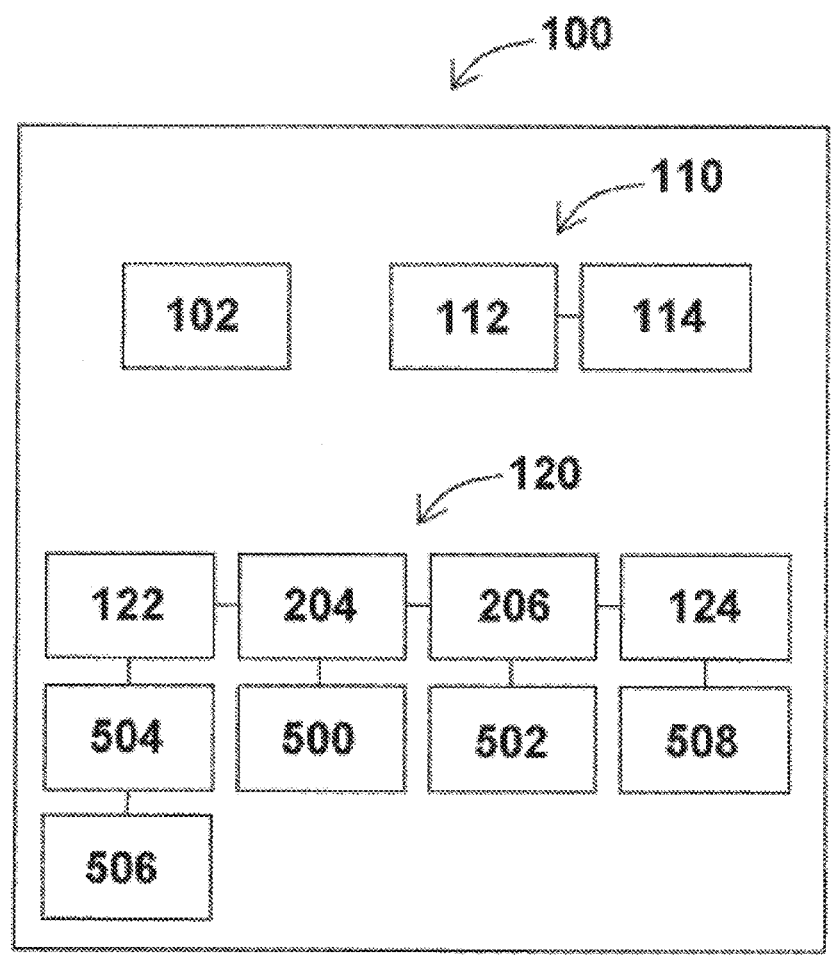
FIG. 5 shows a block diagram of various components of an exemplary thrombus removal system, according to an embodiment of the present disclosure.

An overview of the features, functions and/or configuration of the components depicted in the various figures will now be presented. It should be appreciated that not all of the features of the components of the figures are necessarily described. Some of these non-discussed features, such as various couplers, etc., as well as discussed features are inherent from the figures. Other non discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

An exemplary embodiment of a thrombus removal system of the present disclosure is shown in FIGS. 1B-1D. As shown in FIG. 1B, at least part of a thrombus removal system 100 may be used to penetrate a thrombus 150 (shown alone within a mammalian vessel 152 in FIG. 1A) to facilitate removal of thrombus 150 from a lumen 154 of mammalian vessel 152. A guidewire 102, which may or may not be considered part of a thrombus removal system 100 (depending on the embodiment referenced), may be used to pierce thrombus 150 so that part of guidewire 102 appears proximal to, within, and distal to, thrombus 150. After piercing thrombus 150, guidewire 102 may be advanced so that a distal end 104 of guidewire 102 is distal to thrombus 150 as shown in FIGS. 1B-1D. For purposes of depicting use of guidewire 102 and/or other components of thrombus removal system 100, FIGS. 1A-4C show entry of guidewire 102 and/or other components of thrombus removal system 100 from the left side of mammalian vessel 152.

After insertion of guidewire 102 through thrombus 150, an umbrella catheter 110 (an exemplary component/device of a thrombus removal system 100 of the present disclosure) may be inserted over guidewire 102 so that part of umbrella catheter 110 is positioned proximal to, within, and distal to, thrombus 150, as shown in FIG. 1C. In addition, and also as shown in FIG. 1C, a balloon catheter 120 (another exemplary component/device of thrombus removal system 100 of the present disclosure) may be inserted over umbrella catheter 110 so that part of balloon catheter 120 (having a balloon 122 coupled to a balloon catheter tube 124) is positioned proximal to, within, and distal to, thrombus 150.

After umbrella catheter 110 (and potentially after balloon catheter 120) has/have been positioned, an umbrella 112 of umbrella catheter 110, may be deployed as shown in FIG. 1D. Deployment of umbrella 112 may be performed by, for example, retracting part of umbrella catheter 110, which itself comprises an umbrella catheter tube 116, opposite the initial direction of insertion of umbrella catheter into lumen 154 of vessel 152 so that umbrella 112 may deploy within lumen 154 of vessel 152. For example, a tube 114 of umbrella catheter 110, as shown in FIG. 1D, that initially housed some or all of umbrella 112 therein, may be retracted so that umbrella 112 may expand (which may be, for example, autoexpansion to an open configuration from a compressed configuration within tube 114). In at least another embodiment, advancement of a shaft 116 of umbrella catheter 110, as shown in FIG. 1D, may be performed to push umbrella 112 out of umbrella catheter 110 so that umbrella 112 can deploy within lumen 154 of vessel 152. Umbrella 112, in at least one embodiment, may comprise a mesh, fabric, or other material capable of allowing blood and/or other fluids within lumen 152 to pass therethrough, but preventing some or all of thrombus 150 from passing therethrough as thrombus 150 is disrupted/fractioned from the use of at least part of an exemplary thrombus removal system 100 of the present disclosure. In another embodiment, umbrella 112 may comprise a material that substantially or completely prevents any fluid or material within lumen 154 of vessel 152 from passing therethrough, including portions of thrombus 150.

After at least part of thrombus removal system 100 has been positioned within a vessel 152 (as shown in FIG. 1D), thrombus removal system 100 may be used to, for example, chemically and/or physically remove some or all of thrombus 150. In at least one embodiment of a chemical removal of some or all of thrombus 150 of the present disclosure, at least part of thrombus removal system 100 may be positioned within a thrombus 150 at a desired position (as shown in FIG. 1D and described above and as reproduced in FIG. 2A for convenience), whereby thrombus removal system 100 may be used to introduce one or more chemical agents 200 (depicted as squares within FIG. 2B) local to thrombus 150. Exemplary chemical agents 200 capable of disruption and/or dissolution of at least part of thrombus 150 may include, but are not limited to, one or more tissue plasminogen activators, plasmin, or thrombin, for example. So to avoid undesired exposure of vessel 152 of chemical agents 200 proximal to balloon 122 of balloon catheter 120, balloon 122 may be inflated, as shown in FIG. 2B. In addition, and to avoid undesired exposure of vessel 152 of chemical agents 200 and/or portions of thrombus 150 distal to umbrella 112 of umbrella catheter 110, umbrella 112 may be deployed as shown in FIGS. 2A-2C. Deployment of said umbrella 112, as referenced herein, operates to prevent portions of thrombus 150 from entering the blood stream and potentially forming a damaging, and potentially fatal, clot elsewhere in the body. Chemical agents 200 may be introduced through one or more apertures 202 defined within balloon catheter 120, so that chemical agents 200 from an agent source (not shown) can be introduced through a first lumen 204 of balloon catheter 120, out of aperture(s) 202, and into a lumen 154 of vessel 152. Over time, and as shown in FIG. 2C, chemical agents 200 may disrupt and/or dissolve at least part of thrombus 150, so that thrombus fragments 250 (depicted as circles within FIG. 2C) can break away from thrombus 150 and enter into a second lumen 206 of balloon catheter 120 by way of distal aperture 208. Removal of thrombus fragments 250 may occur via suction through distal aperture 208 of balloon catheter 120, so that thrombus fragments 250 may enter distal aperture 208 as indicated by the arrows shown in FIG. 2C.

In at least one embodiment, and to maintain at least a desired amount of fluid local to the treatment area, saline or another biologically compatible fluid may be introduced through aperture(s) 202, whereby said fluid may also help to flush the treatment area so that a desired amount or level of thrombus fragments 250 are removed from the lumen 154 of mammalian vessel 152.

In at least one embodiment of a physical removal of some or all of thrombus 150 of the present disclosure, at least part of thrombus removal system 100 may be positioned within a thrombus 150 at a desired position (as shown in FIG. 1D and described above and as reproduced in FIG. 3A for convenience), whereby thrombus removal system 100 may be used to introduce disruptive oscillations 300 therethrough (depicted as curved lines within FIG. 3B) local to thrombus 150. Disruptive oscillations 300 may be introduced via ultrasound or one or more other types of physical movement (side-to-side, back-and-forth, and/or in another direction) to increase the shear stress of thrombus 150 to disrupt thrombus 150 and cause portions of thrombus 150 to break away. So to avoid undesired exposure of vessel 152 proximal to balloon 122 of balloon catheter 120 to thrombus fragments 250, balloon 122 may be inflated, as shown in FIG. 3B. In addition, and to avoid undesired exposure of vessel 152 to portions of thrombus 150 distal to umbrella 112 of umbrella catheter 110, umbrella 112 may be deployed as shown in FIGS. 3A-3C. Over time, and as shown in FIG. 3C, disruptive oscillations 300 may disrupt thrombus 150, so that thrombus fragments 250 (depicted as circles within FIG. 3C) can break away from thrombus 150 and enter into a second lumen 206 of balloon catheter 120 by way of distal aperture 208. Removal of thrombus fragments 250 may occur via suction through distal aperture 208 of balloon catheter 120, so that thrombus fragments 250 may enter distal aperture 208 as indicated by the arrows shown in FIG. 3C. In at least one embodiment, and to maintain at least a desired amount of fluid local to the treatment area, saline or another biologically compatible fluid may be introduced through aperture(s) 202, whereby said fluid may also help to flush the treatment area so that a desired amount or level of thrombus fragments 250 are removed from the lumen 154 of mammalian vessel 152.

Removal of a thrombus removal system 100 of the present disclosure from a lumen 154 of a vessel 152 is shown in FIGS. 4A-4C. As shown in FIGS. 4A and 4B, balloon 122 is deflated (shown as partially deflated in FIG. 4A and completely deflated in FIG. 4B) to unsecure thrombus removal system 100 from vessel 152. Pull-back of one or more components of thrombus removal system 100 then causes the deployed umbrella 112 to invert (as shown in the change of orientation from FIG. 4A to FIG. 4B), and further pulling of umbrella catheter 110 back causes umbrella 112 to fit at least partially within distal aperture 208 to facilitate removal of thrombus removal system 100 from the lumen 154 of mammalian vessel 152.

FIG. 5 shows a block diagram of various components of an exemplary thrombus removal system 100 of the present disclosure. As shown in FIG. 5, an exemplary thrombus removal system 100 of the present disclosure may comprise a guidewire 102, an umbrella catheter 110 comprising an umbrella 112 and an umbrella catheter tube 114, and a balloon catheter 120 comprising a balloon 122 and a balloon catheter tube 124. Balloon catheter 120 may define a first lumen 204 therethrough, whereby one or more chemicals and/or a fluid from a substance source 500 can be provided from substance source 500, through the first lumen 204, through one or more apertures 202 defined within balloon catheter tube 124, and into a lumen 154 of a mammalian vessel 152. Balloon catheter 120 may also define a second lumen 206 therethrough, whereby suction from a suction source 502 may be provided through second lumen 206 into lumen 154 of mammalian vessel 152 to remove fluid and/or particulates through distal aperture 208. Balloon catheter 120 may further define a third lumen 504 therethrough, whereby an inflation/deflation source 506 in communication therewith is operable to inflate and/or deflate balloon 122 that is also in communication with third lumen 504. Further, and in at least one embodiment, an oscillator 508 (such as an ultrasound apparatus) may be in communication with one or more components of balloon catheter 120 to introduce disruptive oscillations into a lumen 154 of a mammalian vessel 152.

Figure 6:
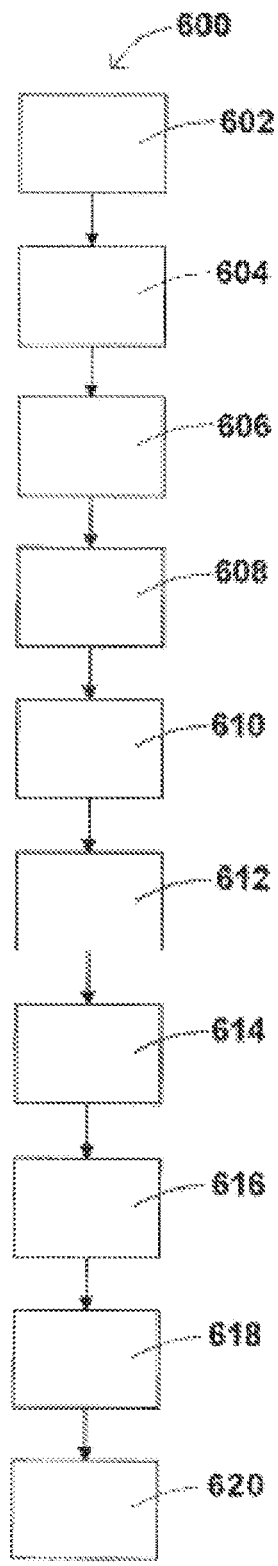
FIG. 6 shows steps of an exemplary method for using an exemplary thrombus removal system to remove a thrombus, according to an embodiment of the present disclosure.

As generally referenced above and as shown in the method step diagram of FIG. 6, an exemplary embodiment of a method of removing a thrombus from a lumen 154 of a mammalian vessel 152 is provided herein. In at least one embodiment of a method 600 of the present disclosure, method 600 comprises the steps of inserting a guidewire 102 into a lumen 154 of a mammalian vessel 152 through a thrombus 150 present therein (an exemplary guidewire insertion step 602), inserting an umbrella catheter 110 through the thrombus 150 around at least part of the guidewire 102 (an exemplary umbrella catheter insertion step 604), and inserting a balloon catheter 120 through the thrombus 150 around at least part of the umbrella catheter 110 (an exemplary balloon catheter insertion step 606). An exemplary method 600 of the present disclosure further comprises the steps of deploying an umbrella 112 of the umbrella catheter 110 to at least substantially occlude the lumen 154 of the mammalian vessel 152 distal to the thrombus 150 or to at least substantially prevent a portion of the thrombus 150 from passing through the umbrella 112 (an exemplary umbrella deployment step 608), inflating a balloon 122 of the balloon catheter 120 to at least substantially occlude the lumen 154 of the mammalian vessel 152 proximal to the thrombus 150 (an exemplary balloon inflation step 610), operating one or more of the umbrella catheter 110 and/or the balloon catheter 120 to disrupt and/or dissolve the thrombus 150 (an exemplary operation step 612), and applying suction through the balloon catheter 120 to remove at least part of the disrupted thrombus 150 from the lumen 154 of the mammalian vessel 152 (an exemplary thrombus removal step 614).

In at least one embodiment of method 600 of the present disclosure, operation step 612 comprises operating the balloon catheter 120 to introduce one or more chemical agents 200 through the balloon catheter 120 into the lumen 154 of the mammalian vessel 152 to disrupt and/or dissolve the thrombus 150. In at least another embodiment, operation step 612 comprises operating one or more of the umbrella catheter 110 and/or the balloon catheter 120 to introduce one or more disruptive oscillations therethrough to disrupt the thrombus 150.

In at least one embodiment of a method 600 of the present disclosure, method 600 further comprises the steps of deflating the balloon 122 (an exemplary balloon deflation step 616) and inverting the umbrella 112 (an exemplary umbrella inversion step 618) so that the umbrella 112 can be positioned at least partially within a distal aperture 208 of the balloon catheter 120, and removing the guidewire 102, the umbrella catheter 110, and the balloon catheter 120 from the lumen 154 of the mammalian vessel 152 (an exemplary system removal step 620).

At least another embodiment of a thrombus removal system 100 of the present disclosure is shown in FIGS. 7A-7C. As shown in FIG. 7A, a guidewire 102 is positioned through a thrombus 150, and a balloon catheter 120 is positioned around at least part of guidewire 102. As shown in FIG. 7A, balloon catheter 120 comprises a first balloon 122 positioned along balloon catheter 120 proximal to thrombus 150, and further comprises a second balloon 700 positioned along balloon catheter 120 distal to thrombus 150. In such an embodiment, balloon catheter 120 may define a lumen 504 in communication with an inflation/deflation source 506, whereby lumen 504 is in communication with first balloon 122 and second balloon 700 to inflate and/or deflate said balloons 122, 700. In at least another embodiment, an additional lumen 702 may be defined within balloon catheter 120, whereby lumen 504 is in communication with first balloon 122 and the additional lumen 702 is in communication with second balloon 700, so that an inflation/deflation source 506 in communication with lumens 504, 702 may inflate and/or deflate balloons 122, 700 separately.

In at least another embodiment of a chemical removal of some or all of thrombus 150 of the present disclosure, at least part of thrombus removal system 100 may be positioned within a thrombus 150 at a desired position (as shown in FIG. 7A), whereby thrombus removal system 100 may be used to introduce one or more chemical agents 200 capable of disruption and/or dissolution of at least part of thrombus 150 (depicted as squares within FIG. 7B) local to thrombus 150. So to avoid undesired exposure of vessel 152 of chemical agents 200 proximal to first balloon 122 of balloon catheter 120, first balloon 122 may be inflated, as shown in FIGS. 7B and 7C. In addition, and to avoid undesired exposure of vessel 152 of chemical agents 200 and/or portions of thrombus 150 distal to second balloon 700, second balloon 700 may also be inflated, as shown in FIGS. 7B and 7C. Chemical agents 200 may be introduced through one or more apertures 202 defined within balloon catheter 120, so that chemical agents 200 from an agent source (not shown) can be introduced through a lumen 204 of balloon catheter 120, out of aperture(s) 202, and into a lumen 154 of vessel 152. Over time, and as shown in FIG. 7C, chemical agents 200 may disrupt and/or dissolve at least part of thrombus 150, so that thrombus fragments 250 (depicted as circles within FIG. 7C) can break away from thrombus 150 and enter into a second lumen 206 of balloon catheter 120 by way of aperture 208. Removal of thrombus fragments 250 may occur via suction through aperture 208 of balloon catheter 120, so that thrombus fragments 250 may enter aperture 208 as indicated by the arrows shown in FIG. 7C.

As generally referenced herein, an "occlusion element" may refer to a balloon catheter 120 with one or more balloons 122, 700, or may refer to an umbrella catheter 110 with one or more umbrellas 112. For example, an exemplary embodiment of a thrombus removal system 100 of the present disclosure may comprise a balloon catheter 120 with a first balloon 122 and an occlusion element, with the occlusion element being either an umbrella catheter 110 with one or more umbrellas 112 (as shown in FIGS. 2B and 2C, for example), or a balloon catheter 120 with a second balloon 700 (as shown in FIGS. 7B and 7C, for example).

In at least another embodiment of a physical removal of some or all of thrombus 150 of the present disclosure, at least part of thrombus removal system 100 may be positioned within a thrombus 150 at a desired position (as shown in FIG. 8A), whereby thrombus removal system 100 may be used to introduce disruptive oscillations 300 therethrough (depicted as curved lines within FIG. 8B) local to thrombus 150. Disruptive oscillations 300 may be introduced via ultrasound or one or more other types of physical movement (side-to-side, back-and-forth, and/or in another direction) to increase the shear stress of thrombus 150 to disrupt thrombus 150 and cause portions of thrombus 150 to break away. So to avoid undesired exposure of vessel 152 proximal to first balloon 122 of balloon catheter 120 to thrombus fragments 250, first balloon 122 may be inflated, as shown in FIGS. 8B and 8C. In addition, and to avoid undesired exposure of vessel 152 to portions of thrombus 150 distal to second balloon 700, second balloon 700 may also be inflated, as shown in FIGS. 8B and 8C. Over time, and as shown in FIG. 8C, disruptive oscillations 300 may disrupt thrombus 150, so that thrombus fragments 250 (depicted as circles within FIG. 8C) can break away from thrombus 150 and enter into a second lumen 206 of balloon catheter 120 by way of aperture 208. Removal of thrombus fragments 250 may occur via suction through aperture 208 of balloon catheter 120, so that thrombus fragments 250 may enter aperture 208 as indicated by the arrows shown in FIG. 8C. In at least one embodiment, and to maintain at least a desired amount of fluid local to the treatment area, saline or another biologically compatible fluid may be introduced through aperture(s) 202, whereby said fluid may also help to flush the treatment area so that a desired amount or level of thrombus fragments 250 are removed from the lumen 154 of mammalian vessel 152.

Removal of an exemplary thrombus removal system 100 of the present disclosure from a lumen 154 of a vessel 152 is shown in FIGS. 9A and 9B. As shown in FIGS. 9A and 9B, balloons 122, 700 are deflated (shown as partially deflated in FIG. 9A and completely deflated in FIG. 9B) to unsecure thrombus removal system 100 from vessel 152 to facilitate removal of thrombus removal system 100 from the lumen 154 of mammalian vessel 152.

Figure 10:
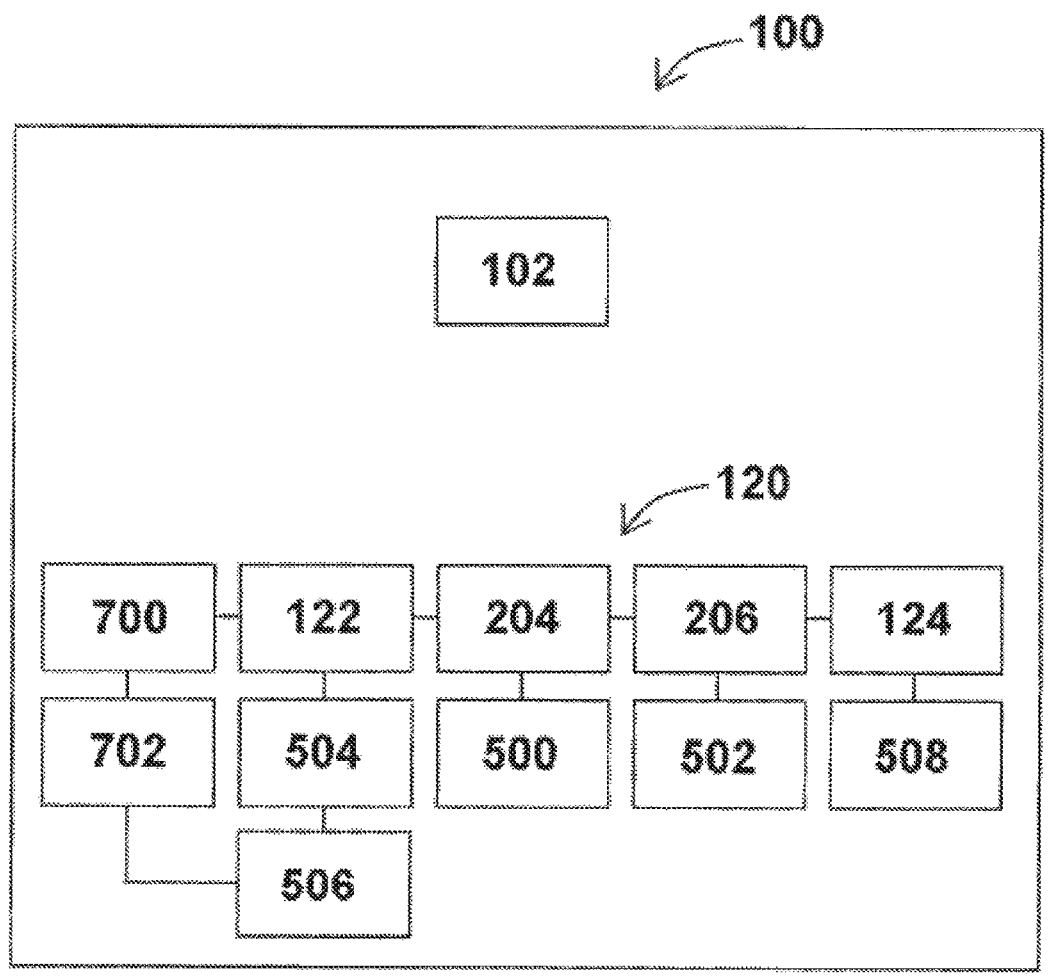
FIG. 10 shows a block diagram of various components of an exemplary thrombus removal system, according to an embodiment of the present disclosure.

FIG. 10 shows a block diagram of various components of another exemplary thrombus removal system 100 of the present disclosure. As shown in FIG. 10, an exemplary thrombus removal system 100 of the present disclosure may comprise a guidewire 102 and a balloon catheter 120 comprising a first balloon 122, a second balloon 700, and a balloon catheter tube 124. Balloon catheter 120 may define a first lumen 204 therethrough, whereby one or more chemicals and/or a fluid from a substance source 500 can be provided from substance source 500, through the first lumen 204, through one or more apertures 202 defined within balloon catheter tube 124, and into a lumen 154 of a mammalian vessel 152. Balloon catheter 120 may also define a second lumen 206 therethrough, whereby suction from a suction source 502 may be provided through second lumen 206 into lumen 154 of mammalian vessel 152 to remove fluid and/or particulates through distal aperture 208. Balloon catheter 120 may further define a third lumen 504 therethrough, whereby an inflation/deflation source 506 in communication therewith is operable to inflate and/or deflate first balloon 122 that is also in communication with third lumen 504. Balloon catheter 120 may further define a fourth lumen 702 therethrough, whereby an inflation/deflation source 506 in communication therewith is operable to inflate and/or deflate second balloon 700 that is also in communication with fourth lumen 702. Further, and in at least one embodiment, an oscillator 508 (such as an ultrasound apparatus) may be in communication with one or more components of balloon catheter 120 to introduce disruptive oscillations into a lumen 154 of a mammalian vessel 152.

Figure 11:
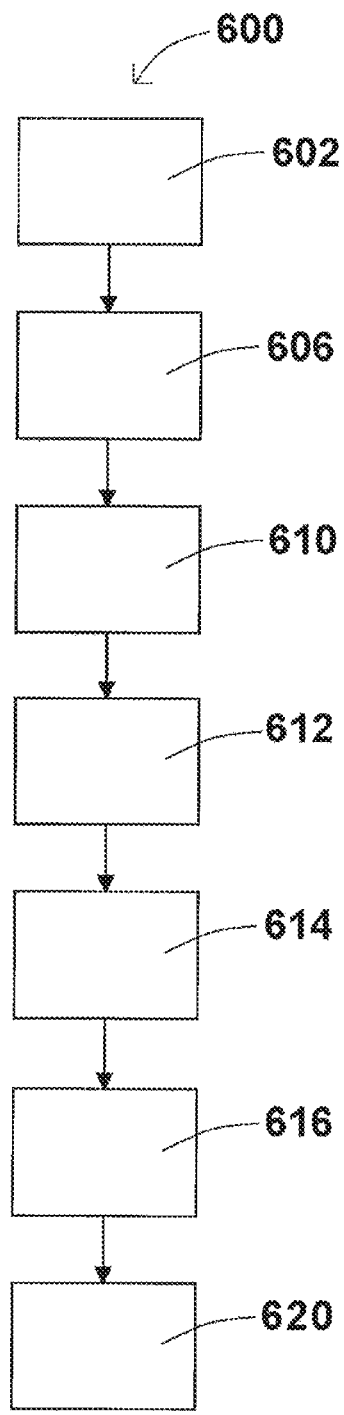
FIG. 11 shows steps of an exemplary method for using an exemplary thrombus removal system to remove a thrombus, according to an embodiment of the present disclosure.

As generally referenced above and as shown in the method step diagram of FIG. 11, another exemplary embodiment of a method of removing a thrombus from a lumen 154 of a mammalian vessel 152 is provided herein. In at least one embodiment of a method 600 of the present disclosure, method 600 comprises an exemplary guidewire insertion step 602, an exemplary balloon catheter insertion step 606, and the step of inflating balloons 122, 700 of the balloon catheter 120 to at least substantially occlude the lumen 154 of the mammalian vessel 152 proximal and distal to the thrombus 150 (another exemplary balloon inflation step 610). In at least one embodiment of method 600 of the present disclosure, method 600 further comprises operating the balloon catheter 120 to disrupt and/or dissolve the thrombus 150 (another exemplary operation step 612) and an exemplary thrombus removal step 614.

In at least one embodiment of method 600 of the present disclosure, operation step 612 comprises operating the balloon catheter 120 to introduce one or more chemical agents 200 through the balloon catheter 120 into the lumen 154 of the mammalian vessel 152 to disrupt and/or dissolve the thrombus 150. In at least another embodiment, operation step 612 comprises operating the balloon catheter 120 to introduce one or more disruptive oscillations therethrough to disrupt the thrombus 150.

In at least one embodiment of a method 600 of the present disclosure, method 600 further comprises the steps of deflating balloons 122, 700 (another exemplary balloon deflation step 616) and removing the guidewire 102 and the balloon catheter 120 from the lumen 154 of the mammalian vessel 152 (another exemplary system removal step 620).

Figure 12:
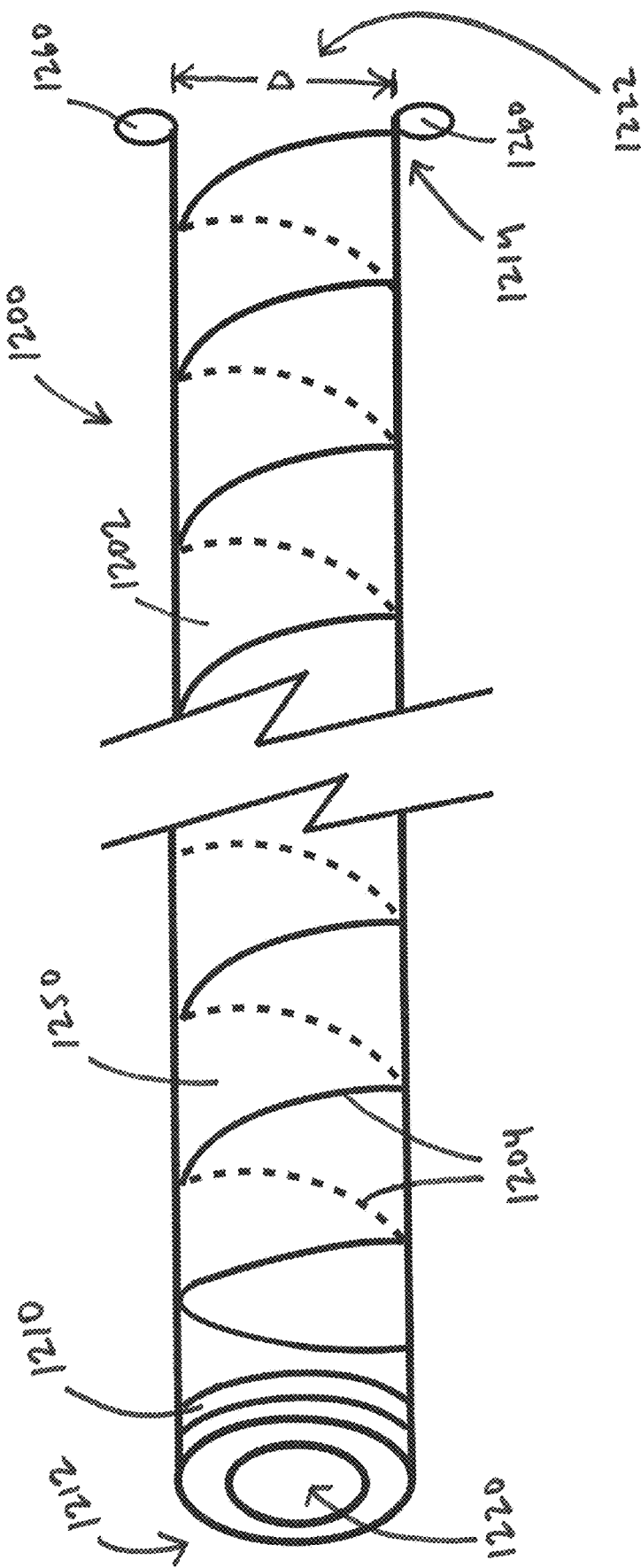
FIG. 12 shows a side perspective view of a thrombectomy sheath, according to an embodiment of the present disclosure.

The present disclosure includes disclosure of additional thrombus removal systems 100. In at least one embodiment, an exemplary thrombus removal system 100 of the present disclosure, as shown in FIG. 12, comprises a thrombectomy sheath 1200 configured as an elongated tube having a circumferential outer wall 1202 reinforced with a reinforcement 1204, such as a wire reinforcement or other reinforcement known or developed in the art, whereby reinforcement 1204 comprises a different material than circumferential outer wall 1202. For example, and in at least one embodiment, circumferential outer wall 1202 comprises a flexible polymer material, while reinforcement 1204 comprises a metallic material. In various embodiments, circumferential outer wall 1202 is very thin, utilizing reinforcement 1204 to prevent collapse or kinking at various bending points of thrombectomy sheath 1200 during use.

As shown in FIG. 12, exemplary thrombectomy sheaths 1200 of the present disclosure may comprise a sonovisible element 1210 at or near a distal end 1212 of thrombectomy sheath 1200. Sonovisible element 1210 may be configured as a ring (as shown in FIG. 12), or comprise a different configuration, such as one or more non-circumferential elements 1210 positioned along or within circumferential outer wall 1202 at or near distal end 1212 of thrombectomy sheath 1200. Sonovisible element 1210 is readily visible within a mammalian vessel 152 when detected from outside a patient using ultrasound and/or fluoroscopy, so that the position of distal end 1212 of thrombectomy sheath 1200 relative to, for example, a puncture site of a vein and/or within the vein, can be located by ultrasound and/or fluoroscopy.

Furthermore, thrombectomy sheaths 1200 of the present disclosure may self-expand (be auto-expandable) so to easier insert the same via venipuncture. In various embodiments, reinforcements 1204 may comprise a metal, nitinol, and/or another material suitable to permit auto-expansion as desired.

Thrombectomy sheaths 1200 of the present disclosure having a relatively large bore, such as having external diameters (measured from an outside of circumferential outer wall 1202, shown as "D" in FIG. 12) of 10 mm, 12 mm, 14 mm, 16 mm, 18 mm, or smaller or larger. In various embodiments, circumferential outer wall 1202 has a 10 mm or a 12 mm diameter and a 25 cm length (from distal end 1212 to proximal end 1214), and in other embodiments, circumferential outer wall 1202 has a 14 mm, 16 mm, or a 18 mm diameter and a 30 cm length (from distal end 1212 to proximal end 1214). The aforementioned sizes/configurations are intended for use, for example, in the popliteal, femoral, or common femoral veins according to the correct fit, noting that an optimal size for a particular patient may be determined by, for example, sizing the vein of entry by ultrasound measurement or other means. Other configurations (diameters and lengths) of thrombectomy sheaths 1200 are also within the scope of the present disclosure.

Figure 13:
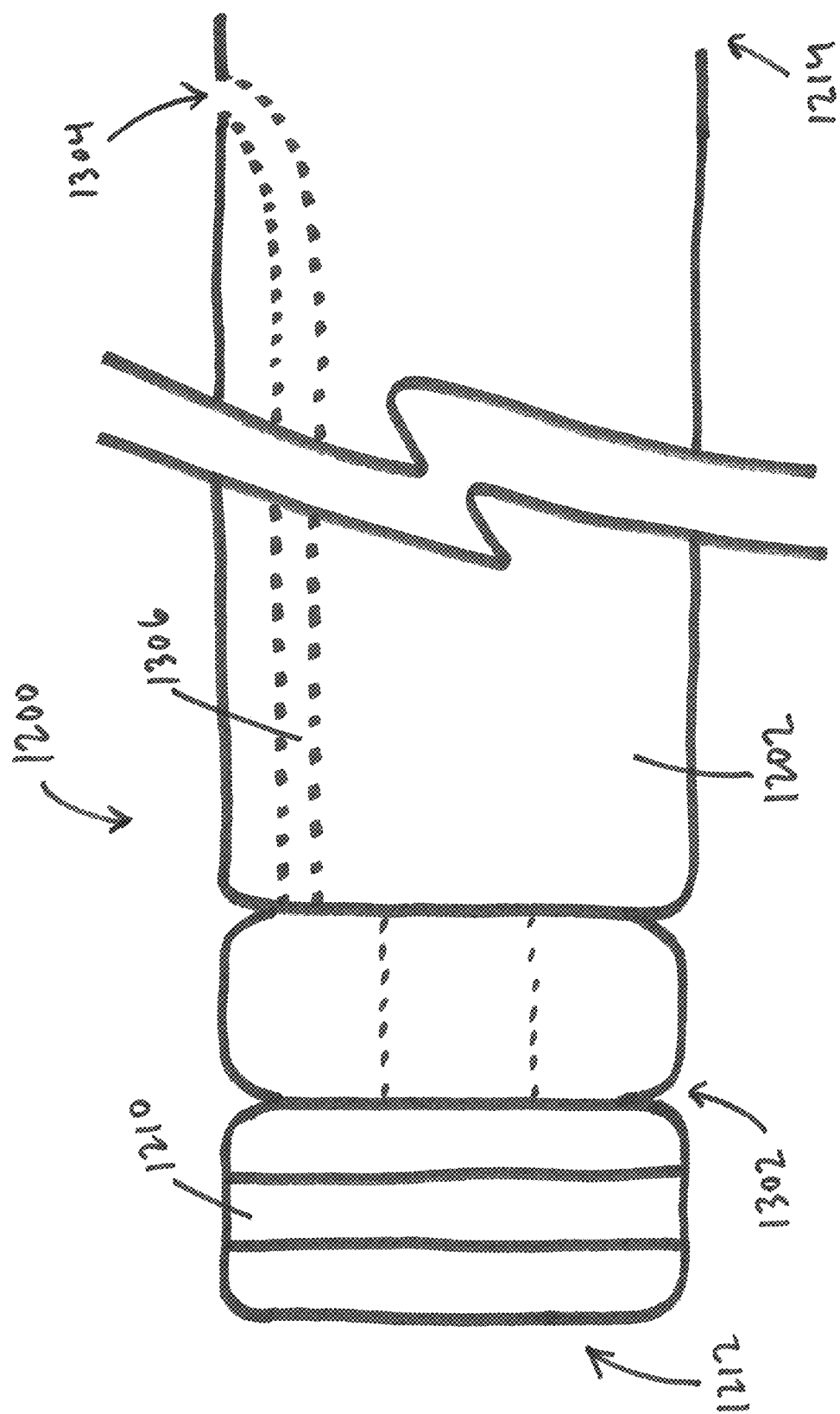
FIG. 13 shows a distal portion of a thrombectomy sheath, according to an embodiment of the present disclosure.

It is noted that in various thrombectomy sheath 1200 embodiments of the present disclosure, a balloon near distal end 1212 of circumferential outer wall 1202 is not used, for simplicity of construction and also because the correct fit of a thrombectomy sheath 1200 to a particular patient would likely prevent any undesired back-bleeding from below the entry site seeping around the thrombectomy sheath 1200. In embodiments of thrombectomy devices 1200 of the present disclosure having a balloon 1300, such as shown in FIG. 13, at least part of balloon 1300 may be positioned at or near distal end 1212 within an indention 1302 defined within circumferential outer wall 1202, so to keep a generally consistent and smooth outer profile of thrombectomy sheath 1200. In such an embodiment, balloon 1300 may be inflated using an inflation/deflation source 506 (not shown in FIG. 13) connected to an inflation/deflation port 1304 of an inflation/deflation channel 1306 extending from balloon 1300 to a location at or near proximal end 1214 of thrombectomy sheath 1200.

Thrombectomy sheaths 1200, in various embodiments, have no valves at or near proximal end 1214, as back-bleeding can be readily controlled by elevating proximal end 1214 above the low venous pressure (when distal end 1212 is positioned within a vein), using a finger, for example, to close proximal end aperture 1222, as shown in FIG. 12, which is opposite distal end aperture 1220 of thrombectomy sheath 1200.

Exemplary systems 100 of the present disclosure may also comprise one or more obturators, as provided in further detail below. In at least one system 100 embodiment, system 100 comprises three obturators having different configurations. A first obturator 1400 may be used for initial introduction, and a second obturator 1500 may be used after a large venipuncture has already been made by or in connection with the initial introduction of part of thrombectomy sheath 1200 into a vein. A third obturator 1700 is used to insert, for example, commercially available biodegradable biostatic sponges over the venipuncture at the end of the procedure. Various obturators 1400, 1500, 1700 of the present disclosure may comprise a soft flexible polymer and/or rubber materials that would conform to a curvature of thrombectomy sheath 1200 once part of thrombectomy sheath 1200 is positioned within a vein.

Figure 14:
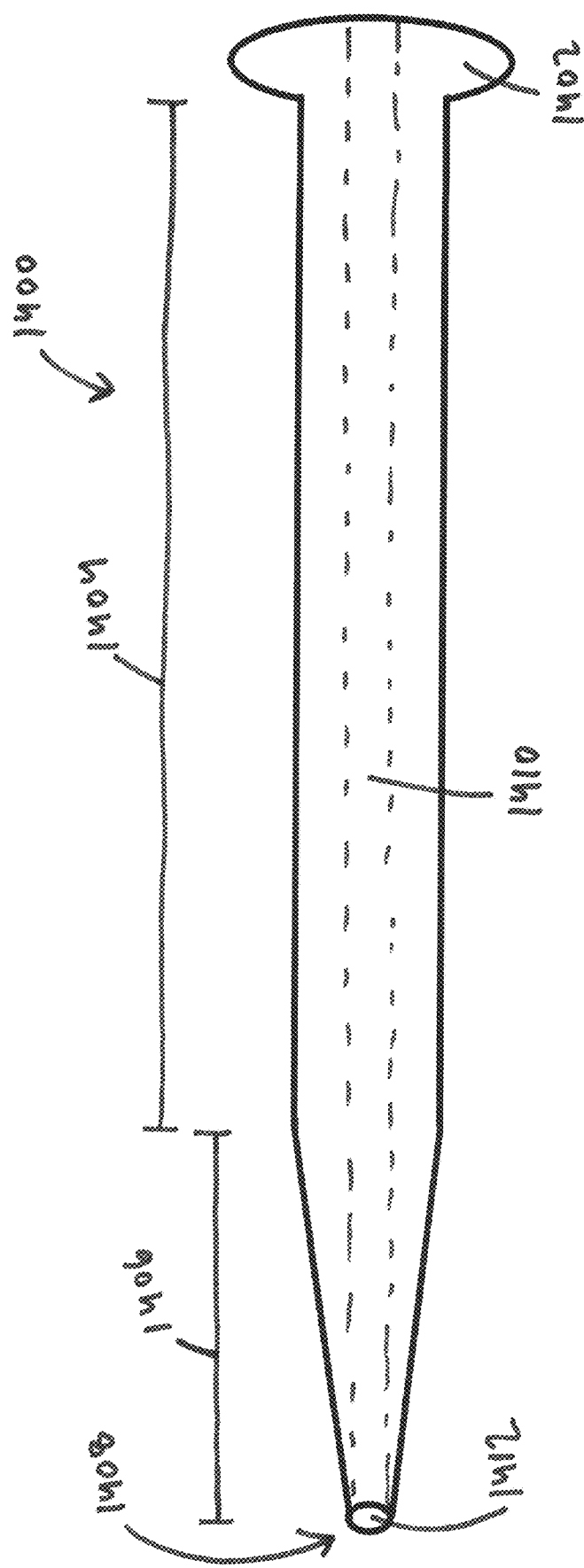
FIG. 14 shows a side view of a first obturator, according to an embodiment of the present disclosure.

FIG. 14 shows an exemplary first obturator 1400 of the present disclosure. As shown in FIG. 14, first obturator 1400 is configured to fit within a lumen 1250 defined within thrombectomy sheath 1200, so that first obturator 1400 fits snugly therein. First obturator 1400 may comprise a flange 1402, which may be configured as a beveled ring or other configuration having a larger cross-section than a general diameter of the elongated portion 1404 of first obturator 1400, which is configured to engage or couple to (such as to snap in or otherwise mate to) a proximal coupler 1260 of thrombectomy sheath 1200. A tapered portion 1406 at a distal end 1408 of first obturator 1400 allows for relatively smooth introduction of distal end 1408 into a vein (an exemplary mammalian vessel 152) as it is advanced over a guidewire 102 (not shown in FIG. 14) so to dilate the vein. In at least one embodiment, tapered portion 1406 projects 7 cm or more or less beyond thrombectomy sheath 1200. A guidewire channel 1410 is defined along a length of first obturator, ending with a distal end aperture 1412, and configured to receive a guidewire 102 having various diameters, such as up to 0.035" or more.

Figure 15:
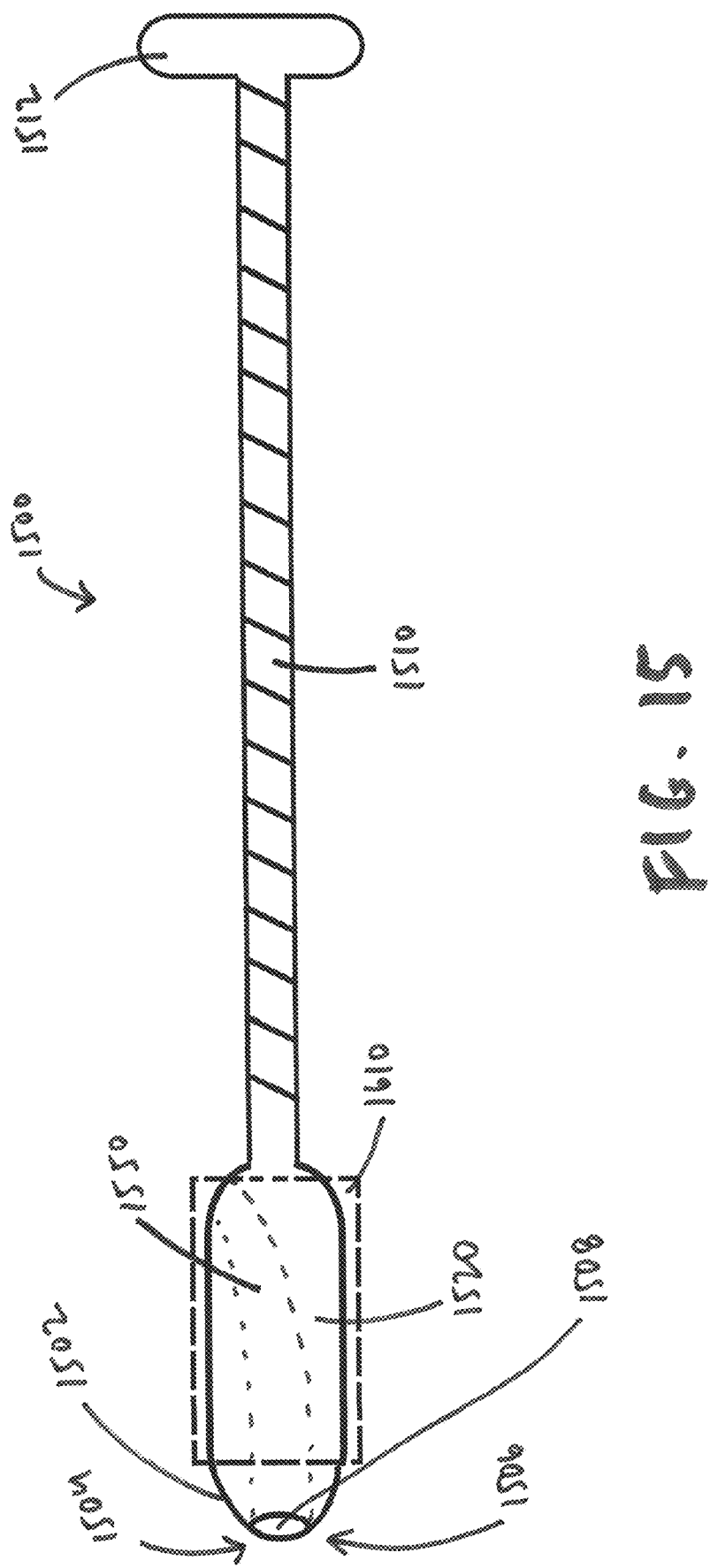
FIG. 15 shows a side view of a second obturator, according to an embodiment of the present disclosure.
Figure 16B:
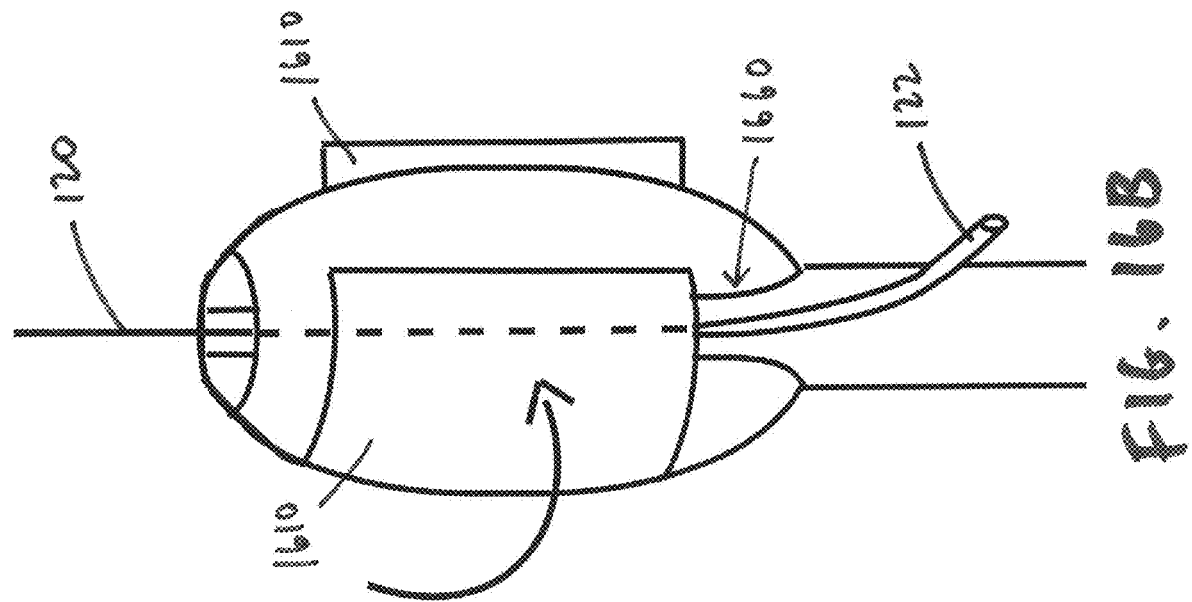
FIG. 16B shows a distal portion of a second obturator with a fitting ring in a closed configuration, according to an embodiment of the present disclosure.
Figure 16A:
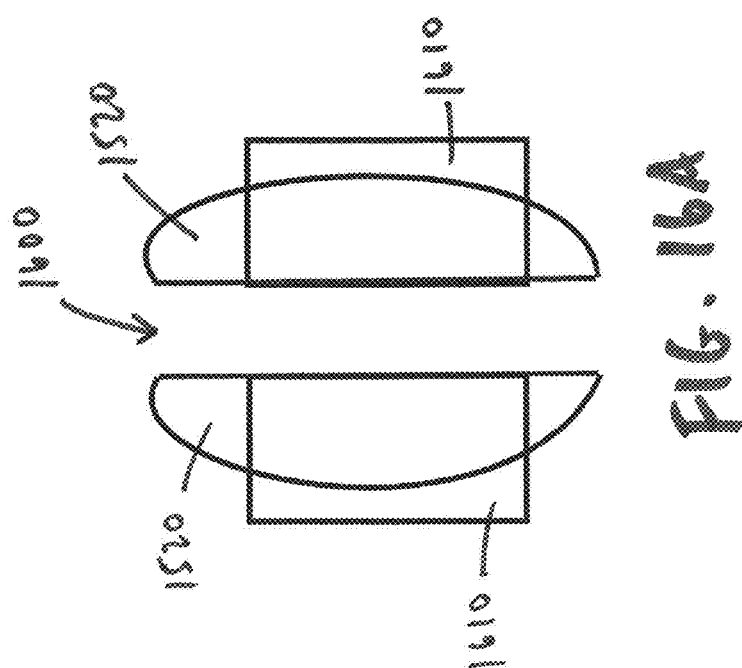
FIG. 16A shows a distal portion of a second obturator with a fitting ring in an open configuration, according to an embodiment of the present disclosure.

An exemplary second obturator 1500 of the present disclosure is shown in FIG. 15. Second obturators 1500 of the present disclosure are generally shorter than first obturators 1400 of the same system 100, projecting 3 cm (or more or less in various embodiments) beyond distal end 1212 of thrombectomy sheath 1200 when positioned therein. As shown in FIG. 15, second obturators 1500 have a rapid taper 1502 near a distal end 1504 of second obturator 1500, terminating at a smoothed tip 1506. Second obturator 1500, as shown in FIG. 15, comprises an elongated portion 1510 extending from a flange 1512 (an effective handle for a user of second obturator 1500) to a cylindrical portion 1520, which can be 4 cm in length (or longer or shorter), configured for a relatively snug fit when positioned within lumen 1250 of thrombectomy sheath, and whereby distal end 1504 of second obturator extends at or about 3 cm (or more or less) from distal end 1212 of thrombectomy sheath. Distal end 1504 of second obturator 1500 terminates at a distal end aperture 1508. Cylindrical portion 1520 has a larger diameter or cross-sectional area as compared to elongated portion 1510, as shown in FIG. 15. A groove 1600 (which may be hemi-cylindrical) is defined within cylindrical portion 1520, as shown in FIG. 16A, which can occupy half the circumference (or more or less) of lumen 1250 of thrombectomy sheath 1200 when positioned therein, allowing space for guidewires 102, balloon catheters 120, or snares 2102 (shown in FIG. 21, for example) to lie beside or within cylindrical portion 1520 unhindered. A hemi-circular fitting ring 1610, as shown in FIGS. 15, 16A, and 16B, fits upon cylindrical portion 1520 and is configured to rotate thereon so to effectively lock portions of guidewires 102, balloon catheters 120, or snares (not shown), etc., therein as shown in FIG. 16B. Such a fitting ring 1610 (also referred to as a locking sleeve) can snap onto portions of second obturator 1510 to retain the same thereon, leaving space for the aforementioned guidewires 102, balloon catheters 120, snares, or other items to exit distal end aperture 1200 of thrombectomy sheath 1200.

Smoothed tip 1506 and cylindrical portion 1520 of second obturator 1500 noted above define a central channel 1550, such as shown in FIG. 15, which can be 8 Fr. or larger or smaller in size, such as to accommodate a 6 Fr. balloon catheter 120, for example. Existing guidewires 102, balloon catheters 120, or snares 2102 entering the vein already can be side loaded into central channel 1550 by gently forcing them through longitudinal groove 1600 running the entire length of cylindrical portion 1520. If rubber (or material with similar properties) is used, groove 1600 may spontaneously close behind these inserted items, retaining them within central channel 1550. If second obturator 1500 is made of polymer, for example, a fitting ring 1610 can be used to retain guidewires 102, balloon catheters 120, snares 2102, etc., within cylindrical portion 1520. Once central channel 1550 is loaded with guidewires 102, balloon catheters 120, snares 2102, etc., fitting ring 1610 can be twisted/rotated to retain these items within central channel 1550, as shown in FIG. 16B. Fitting rings 1610, in various embodiments, can extend from near the tip of the cone (distal end 1504) to a relative top 1660 of the cylindrical portion 1520.

Regarding reintroduction of a thrombectomy sheath 1200 that is pulled purposefully or accidentally out of the vein, a second obturator 1500 can be used to load one or more guidewires 102, balloon catheters 120, or snares 2102 (still in the vein) through groove 1600 above thrombectomy sheath 1200. Second obturator 1500 can then be slid into lumen 1250 of thrombectomy sheath 1200, sliding over the loaded items and into the vein through the previously made large venipuncture, where thrombectomy sheath 1200 itself can then follow suit. Second obturator 1500 can then be removed, unloading the contents of central channel 1550 from groove 1600.

Regarding the introduction of a new or fresh thrombectomy sheath 1200 to remove a large foreign body (such as a burst angioplasty balloon 122 that has detached partially from the stem, or various other items within a vessel 152 such as a vein), a relative back end of balloon catheter 120 can be cut, removing any applicable balloon 122 inflation and/or irrigation ports. This would result in a smooth catheter end over which the existing small sheath can be removed. The relatively larger thrombectomy sheath 1200 with second obturator 1500 can then be introduced over the catheter (remainder of balloon catheter 120) into the vein. The relatively large caliber of thrombectomy sheath 1200 allows much easier and quicker retrieval of the foreign body than is possible through smaller sheaths that are typically used for balloon angioplasty or stenting applications. The large thrombectomy sheath 1200 can also be used over existing guide wires 102 (of or within first obturator 1400 and/or second obturator 1500) to snare displaced stents, filters etc.

Figure 17:
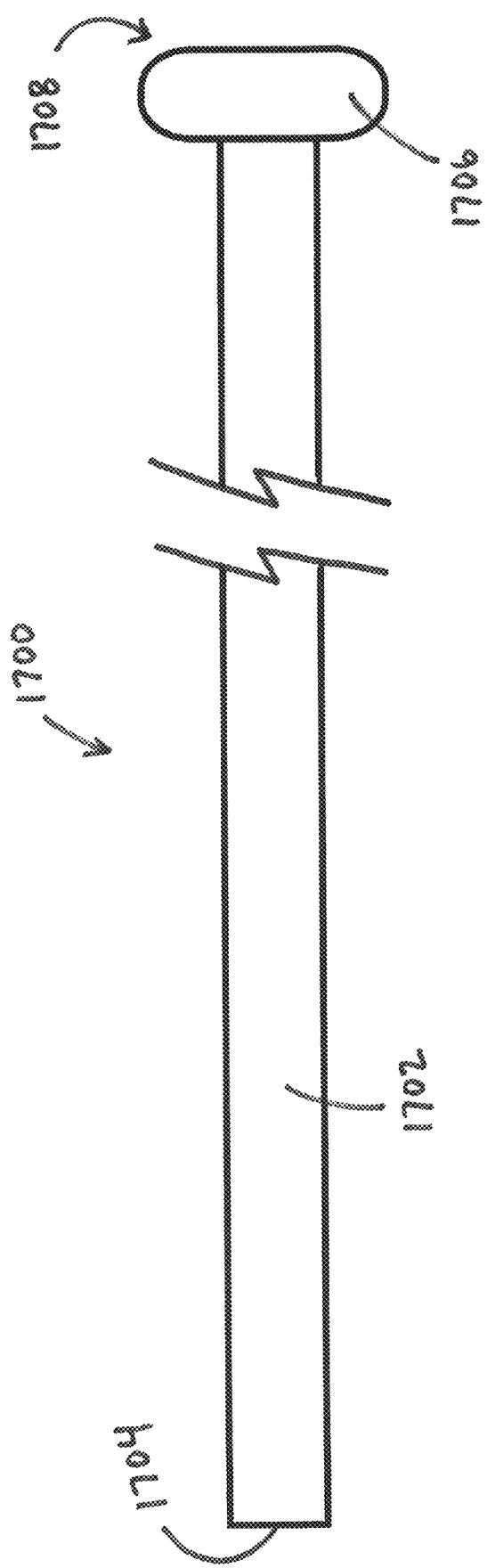
FIG. 17 shows a side view of a third obturator, according to an embodiment of the present disclosure.

FIG. 17 shows an exemplary third obturator 1700 of the present disclosure. Third obturator 1700, as shown in FIG. 17, comprises a generally uniform cylinder 1702 with a flat tip 1704 extending 2 cm or more or less from distal end 1212 of thrombectomy sheath 1200 when positioned therein. A handle 1706 positioned at a proximal end 1708 of third obturator 1700 can be used as a grip by the user of third obturator 1700.

FIGS. 18A and 18B show exemplary ancillary dilators 1800 of the present disclosure. Ancillary dilators 1800 can comprise various sizes, such as 10 Fr., 14 Fr., 16 Fr., 20 Fr., 24 Fr., 28 Fr. or other larger or smaller sizes, and may be 10" or longer or shorter in length. Ancillary dilators 1800 may comprise a similar construction and/or features as exemplary second obturators 1500 of the present disclosure, comprising an elongated body 1802 and a relatively larger ovular portion 1810 having a pointed tip 1820 (in various embodiments), defining a groove 1600 therein that can be side loaded (as noted above in connection with second obturator 1500 embodiments), whereby groove 1600 is either self-closing (where portions of ancillary dilators 1800 comprise rubber or a similar material) or by using a fitting ring 1610 also referred to as a locking sleeve, and such as used with polymer-based ancillary dilators 1800,) to retain guidewires 102, balloon catheters 120, etc., within said groove 1600. Various ancillary dilators can have an ovular portion 1810 approximately 2 cm in length (or longer or shorter), with a 2 cm long (or longer or shorter) groove 1600, whereby part of groove 1600 defines and/or terminates at a central channel 1550. Ancillary dilators, such as shown in FIGS. 18A and 18B, can have a more gentle (gentler) tapered portion 1860 as compared to blunt taper 1502 of an exemplary second obturator, such as shown in FIG. 15. While cylindrical portion 1520 is convenient when used within thrombectomy sheath 1200, it can potentially snag into the tissues during withdrawal when used alone as a dilator. As such, using one or more ancillary dilators 1800 will not snag due to the smooth taper 1860 of ovular portion 1810.

Ancillary dilators 1800 are useful to dilate a small venipuncture opening, such as when a smaller sheath had been used initially. This allows successful introduction of a thrombectomy sheath 1200 for thrombus 150 and/or other foreign body removal.

Figure 19:
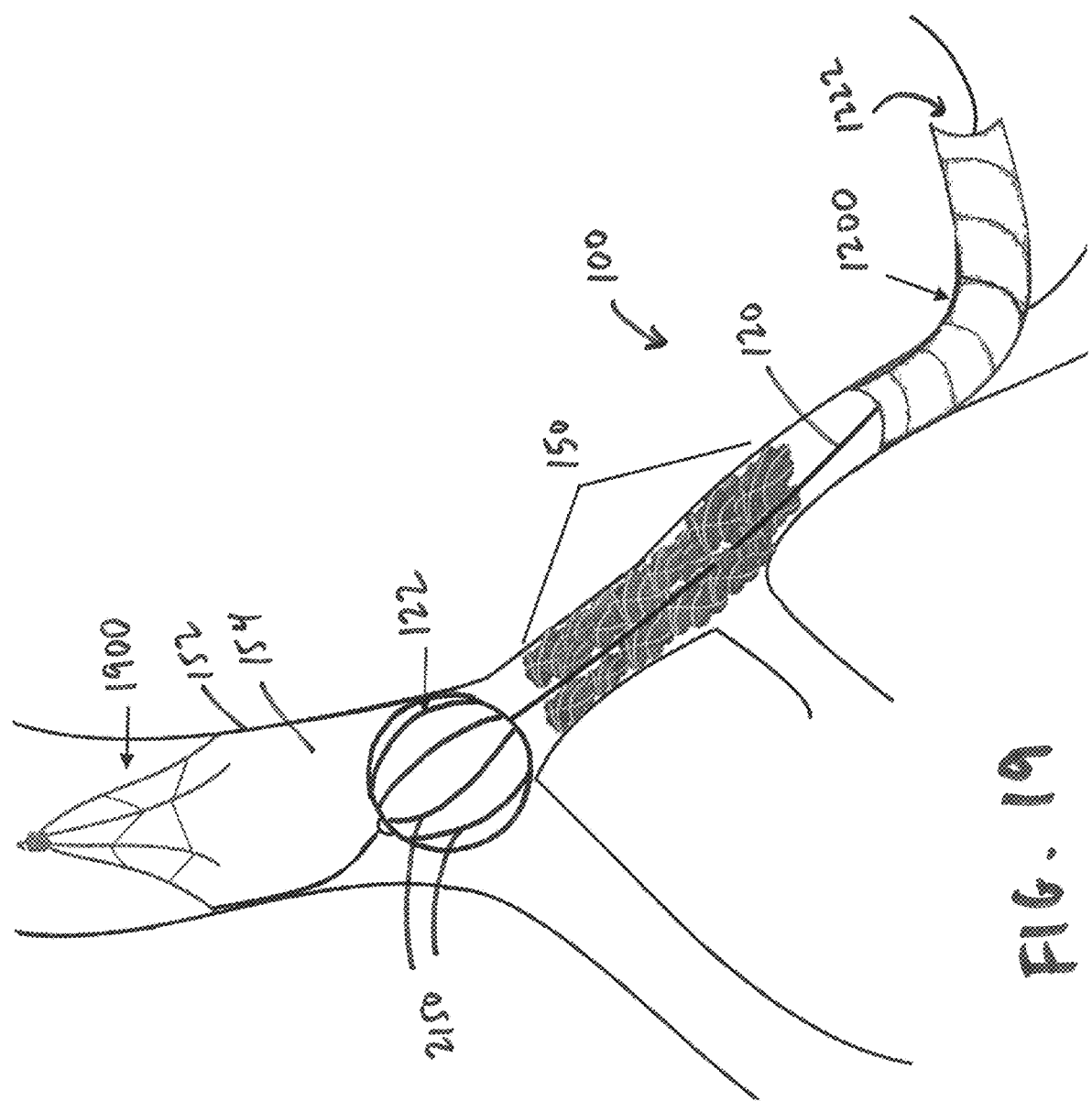
FIGS. 19 and 20 show portions of systems used to remove clots, according to embodiments of the present disclosure.
Figure 20:
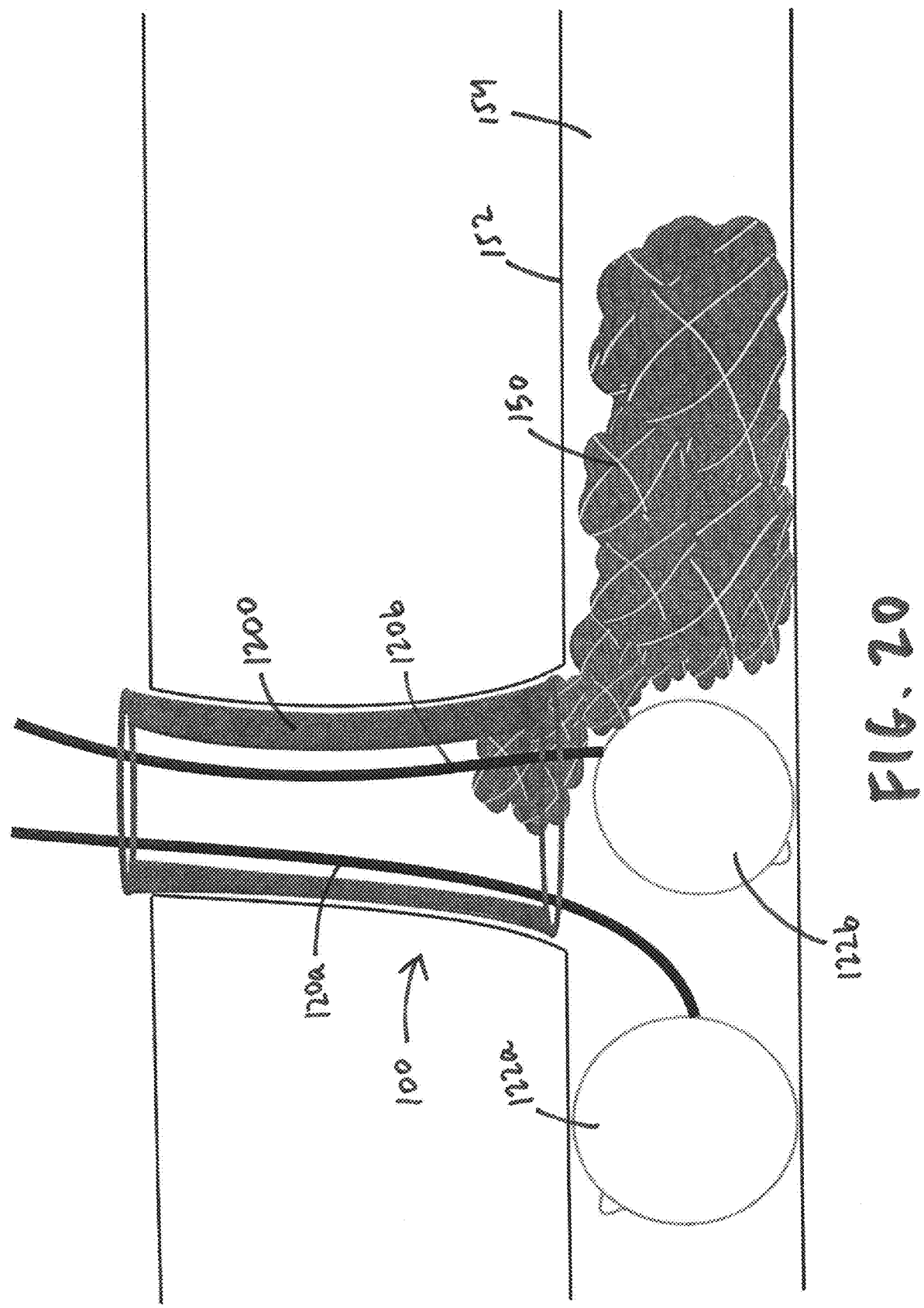

FIGS. 19 and 20 show use of an exemplary thrombectomy sheath 1200 and potentially other system 100 components within a vein in attempt to clear a thrombus 150 therefrom. As shown in FIGS. 19 and 20, one or more thrombectomy balloons (exemplary balloons 122 of the present disclosure) may be used, such as Fogarty balloons, are semi-compliant that can be threaded over a guidewire 102, such as a 0.035" guidewire 102. Balloon catheter 120 shaft and/or balloon 122 can comprise a material with hydrophilic coating that slides easily inside the end loading and side loading obturators 1400, 1500, described above. Radio-opaque marker rings 2150, such as shown in FIGS. 19 and 22, identify the tip and upper and lower ends of the balloon 120.

Use of an exemplary system 100 comprising a thrombectomy sheath 1200 of the present disclosure for percutaneous thrombectomy is as follows. As will be discussed in detail, the present disclosure uses a large bore thrombectomy sheath 1200 and extraction of a clot (thrombus) using one or more balloons 122. Balloons 122, such as 6 Fr. or 8 Fr. Fogarty balloons, can be used with it withdrawing large amounts of thrombus 150. Balloon 122 is likely to result in less injury to red cells in the circulation than with thrombus 150 pulverizing devices (less potential red cell damage and hemoglobinuria). No saline injection is necessary when performing such a method.

Systems 100 can also be used to retrieve foreign bodies such as partially or fully inflated balloons 122, and misplaced stents, filters 1900, etc., more easily than with existing devices used in the medical arts. Use of thrombectomy sheaths 1200 of the present disclosure, as generally referenced herein, allows for a closed percutaneous procedure for thrombectomy.

As shown in FIG. 19, an initial temporary inferior vena cava (IVC) filter 1900 can be inserted well above thrombus 150 through a preferred access site (contralateral or the same site to be used for thrombectomy, or via the internal jugular vein, for example). Filter 1900 can then be removed at the end of the procedure or later as desired.

Ipsilateral, popliteal, femoral, or common femoral vein access is obtained as indicated by the extent of thrombus 150. An initial sheath (not shown in FIG. 19), which may be 11 Fr. or larger or smaller, is initially introduced over a guidewire 102 (such as a 0.035" hydrophilic coated guidewire, for example) to perform a venogram to assess the location and extent of thrombus 150. A thrombectomy sheath 1200 (which may be properly sized by ultrasound measurement of the accessed vein) is then introduced over the guide wire 102 using a first obturator 1400 in a single pass or after passage of serial ancillary dilators 1800 as referenced above.

First obturator 1400 is removed, and back-bleeding through thrombectomy sheath, if any, is controlled by elevating the proximal end 1214 of thrombectomy sheath 1400 above venous pressure and/or plugging proximal end aperture 1222 with a finger beside guidewire 102 or Fogarty catheter (an exemplary balloon catheter 120 having a Fogarty balloon (an exemplary balloon 122 of the present disclosure). Blood from below the insertion site seeping around thrombectomy sheath 1200, if any, can be controlled by a sterile occlusive pneumatic cuff (not shown) placed around the limb immediately below the entry site of thrombectomy catheter 1200.

Figure 21:
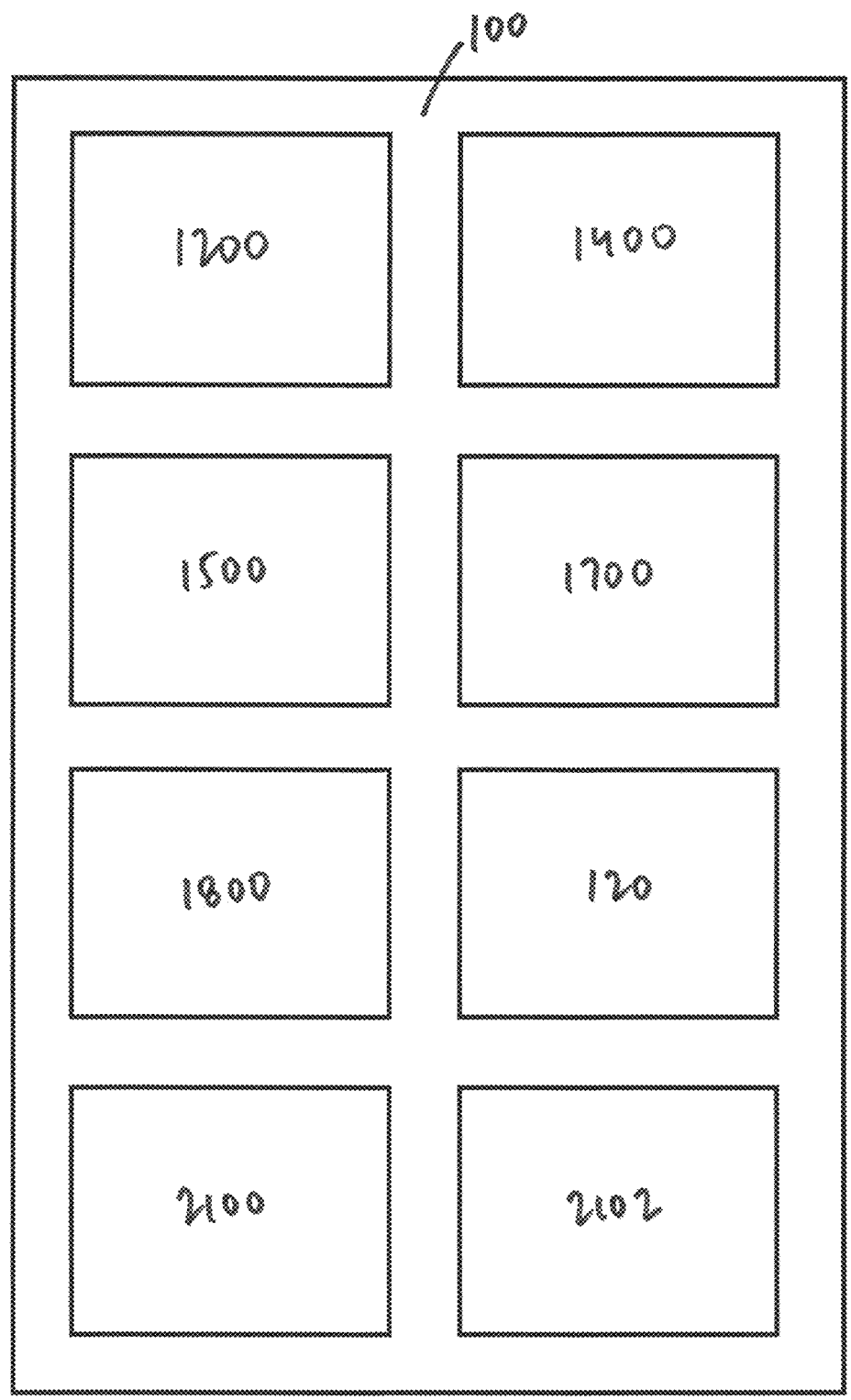
FIG. 21 shows a block component diagram of a system, according to an embodiment of the present disclosure.

A 6 or 8 Fr. specially coated Fogarty catheter (an exemplary balloon catheter 120) can then be introduced and advanced, with the Fogarty balloon (an exemplary balloon 122) inflated above the clot (thrombus 150). An inflating syringe (an exemplary inflation/deflation source 506 as referenced herein) connected to balloon catheter 120 can be hand-controlled, allowing a sense of pressure to be felt within balloon 120 as it is withdrawn over varying lumen sizes. Balloon 122 can be further inflated or deflated as dictated by the "feel" of balloon 122 as it is withdrawn, noting that open thrombectomy using a Fogarty balloon 122 may have a similar technique. FIG. 19 shows use of a thrombectomy sheath 1200, balloon catheter 120 (having balloon 122), within a lumen 154 of a vein (vessel 152), as noted herein. Thrombus 150 can then be withdrawn into thrombectomy sheath 1200 and pulled out the back end via proximal end aperture 1222. Multiple back and forth passes (such as 2 or 3 or more) of balloon catheter 120 may be required until no further thrombus is retrieved, which can generally be achieved by advancing a distal part of balloon catheter 120 with a deflated balloon 122 into and through thrombus 150, inflating balloon 122, pulling balloon catheter 120 back toward thrombectomy sheath 1200, deflating balloon 122, and repeating the process as often as desired. Back bleeding after removal of thrombus 150 can be digitally controlled as described herein, or by balloon tamponade, for example, with the Fogarty balloon (balloon 122). If thrombectomy sheath had been inserted below the lower extent of thrombus 150, for example, the procedure may be complete after performing a completion IVUS or venogram through an irrigation catheter (not shown) inserted into the thrombectomy sheath 1200. Thrombectomy sheath 1200 can now be pulled back just outside the venipuncture into the tissues under ultrasound/fluoroscopy guidance, for example. A hemostatic plug 2100 (Ivalon, Gelfoam, Surgicell, or similar), such as indicated in FIG. 21, can be inserted into the back end of thrombectomy sheath 1200 (such as via proximal end aperture 1222) and pushed toward and out of distal end aperture 1220 using third obturator 1700 having a flat tip 1704 into the tissues immediately overlying the venipuncture site.

If the thrombectomy sheath 1200 had been inserted into thrombus 150, only the upper portion had been cleared and some will remain in the vein below the venipuncture. The following procedure can be used to clear that residual thrombus 150:

A second hydrophilic coated guide wire (exemplary guide wire 102) is now passed up the vein. Thrombectomy sheath 1200 can then be pulled back just enough to exit the venipuncture site and lie immediately outside in the tissues. This can be performed with the aid of ultrasound and fluoroscopy monitoring the position of the locator ring (sonovisible element 1210) at or near the distal end 1212 of thrombectomy sheath 1200. Ultrasound imaging would show, for example, the vein (vessel 152) dropping back from thrombectomy sheath 1200 as it exits the venipuncture. A first Fogarty catheter (balloon catheter 12, identified as 120*a* in FIG. 20) can be positioned 3 cm (or further or nearer) above the venipuncture (with fluoroscopy aid) and can be left with a first balloon 122 (identified as 122*a* in FIG. 20) inflated to control back bleeding from segments of vein (vessel 152) above the venipuncture cleared of thrombus 150.

A second standard 5 Fr Fogarty catheter (another exemplary balloon catheter 120, identified as 120*b* in FIG. 20) can be threaded over the second guide wire 102 and be positioned with a second balloon 122 (identified as 122*b* in FIG. 20) inflated just below the first specially coated Fogarty balloon 122*a* left inflated to control back bleeding, such as shown in FIG. 20. The inflated parked balloon 122*a* also prevents the lower thrombus 150 from travelling up the vein as it is extracted. A bandage (such as an Esmarch bandage, not shown) can be tightly applied starting at the foot level and wound around the leg up to the point of the skin entry of thrombectomy sheath 1200, for example. Elevation of the leg can also help this process. The Esmarch bandage can squeeze the residual thrombus 150, exiting the venipuncture. Thrombus 150 can be removed through thrombectomy sheath by pulling the inflated second Fogarty balloon (such as a 5 Fr. balloon 120, shown as 122*b* in FIG. 20). A hydrophilic coating of the special Fogarty catheter (catheters 120*a* and/or 120*b* and/or components thereof, such as balloons 122*a* and/or 122*b*) and the guidewires 102 (as applicable/desired) allow the second Fogarty balloon (balloon 122*b*), for example, to slide easily beside them pushing them to the periphery of thrombectomy sheath 1200 as thrombus 150 is extracted. Several "passes" of the second balloon 122*b* may be required for complete thrombus 150 clearance, using the same or a similar process as described above in connection with FIG. 19 (advancement, inflation, retraction, deflation, etc.). After all or substantially all extruded thrombus 150 is extracted, the parked first coated Fogarty catheter balloon 122*a* is pulled down to the venipuncture extracting any remaining thrombus 150 trapped in the vein between the Fogarty balloon 122*a* and the venipuncture. The Fogarty catheter 120*a* can then be removed. Bleeding through the venotomy and thrombectomy sheath 1200 at this stage can be controlled by compressing the vein by the sheath tip positioned immediately outside the venotomy. At this point a completion IVUS or venogram can be performed and the two guidewires 102 in the vein can be removed. Next, thrombectomy sheath can be removed after inserting hemostatic plug 2100, for example, as described above.

The present disclosure also includes disclosure of removing a partially detached angioplasty balloon, stent, or other foreign body using thrombectomy sheath 1200. For example, a guidewire 102, balloon catheter 120 stem or loop, etc., in place inside the vein when the mishap had occurred should be retained. Typically, a relatively small sheath (10 Fr. or smaller, for example) would have been used. This small sheath should be removed cutting of ports and side arms of the balloon catheter 120 to slide the small sheath over the back end. Side loading dilators can be optionally used to enlarge the venipuncture site at this point. If only a guide wire 102 is present, a thrombectomy sheath (such as the largest allowable for the vein; 2 mm oversizing of thrombectomy sheath 1200 can be well tolerated) with a first obturator 1400 can be used to introduce thrombectomy sheath 1200 in a single pass. If larger balloon catheters 120 or snares 2102 are present, a second obturator 1500 could be used side-loading it as described above. Partially detached (usually at the lower end) balloons 122, even if the balloon 122 had 'bunched up' due to invagination or eversion ('parachuted') can be retrieved through the large thrombectomy sheath 1200 by pulling on the balloon catheter 120 stem. If the balloon 122 is completely detached, such as shown in FIG. 22, it can be easily retrieved by a loop 2104 of snare 2102 through the large lumen thrombectomy sheath 1200. Many types of misplaced stents and filters 1900 can also be retrieved with standard techniques through the large thrombectomy sheath 1200.

Thrombectomy sheaths 1200 of the present disclosure, as described herein, are relatively simple devices and are expected to perform well clinically as established techniques are used. FIG. 21 shows a block component diagram of exemplary components of a system 100 of the present disclosure, noting that any number of system 100 embodiments may include one or more of the various components shown therein and/or otherwise described herein.

An additional thrombectomy sheath 1200 embodiment is shown in FIG. 23. As shown in FIG. 23, thrombectomy sheath 1200 comprises a flared distal end 1212 comprising a flared portion 2300 having a cross-section larger than that of circumferential outer wall 1202 proximal to flared portion 2300. Such a configuration permits a larger thrombus 150 to enter lumen 1250 of thrombectomy sheath 1200 than may otherwise be possible without flared portion 2300. Various thrombectomy sheaths 1200 of the present disclosure may further comprise a fragmenter 2310, such as one or more blades, spines, etc., configured to at least partially fragment thrombus 150 as it passes through thrombectomy sheath 1200 for ease of potential extraction therefrom.

Various thrombus removal systems 100 of the present disclosure may comprise components known in the catheter arts, such as biologically-compatible plastics, rubber, stainless steel, and the like.

While various embodiments of thrombus removal systems and devices and methods of using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A thrombectomy system, comprising:
   a thrombectomy sheath, comprising:
   a circumferential outer wall reinforced with a reinforcement, configured as an elongated tube having a lumen therethrough; and
   a sonovisible element positioned at or near a distal end of the circumferential outer wall;
   wherein the thrombectomy sheath is sized and shaped to be at least partially positioned within a vein proximal to a thrombus or other item within the vein and further configured to expand to contact the vein to secure the thrombectomy sheath within the vein; and
   wherein the lumen is sized and shaped to receive a device selected from the group consisting of a balloon catheter and a snare having a loop; and
   a first obturator comprising an elongated portion and a cylindrical portion at a distal end of the first obturator having a larger diameter than the elongated portion, the cylindrical portion comprising a longitudinal groove defined therein configured to be self-closing.

2. The thrombectomy system of claim 1, wherein the circumferential outer wall comprises a flexible polymer material, and wherein the reinforcement comprises a metallic material.

3. The thrombectomy system of claim 1, wherein the circumferential outer wall is configured for autoexpansion.

4. The thrombectomy system of claim 1, further comprising:
   a balloon positioned at or near a distal end of the circumferential outer wall, at least partially positioned within an indention defined within the circumferential outer wall.

5. The thrombectomy system of claim 1, further comprising:
   a second obturator configured to fit within the lumen of the thrombectomy sheath, the second obturator comprising a flange configured to engage a proximal coupler of the thrombectomy sheath and defining a tapered portion at a distal end, the tapered portion configured to extend from the distal end of the thrombectomy sheath so to dilate the vein when advanced therein.

6. The thrombectomy system of claim 1,
   wherein the longitudinal groove is configured to receive at least part of the balloon catheter, and self-closes so to lock at least part of the balloon catheter within the longitudinal groove.

7. The thrombectomy system of claim 5, further comprising:
   a third obturator comprising a generally uniform cylinder having a flat tip, the third obturator configured to extend at least 2 cm from the distal end of the thrombectomy sheath when positioned therein.

8. The thrombectomy system of claim 5, further comprising:
   an ancillary dilator comprising an elongated portion and an ovular portion larger than the elongated portion of the ancillary dilator and having a pointed tip and defining a groove therein configured to receive at least part of a balloon catheter therein, and further comprising a fitting ring configured to fit upon the relatively larger ovular portion and rotate thereon so to lock at least part of the balloon catheter within the groove.

9. The thrombectomy system of claim 1, further comprising the balloon catheter.

10. The thrombectomy system of claim 7, further comprising:
    a hemostatic plug configured to be pushed through the lumen of the thrombectomy sheath using the flat tip of the third obturator so that the hemostatic plug is positioned within the vein after being pushed out of the thrombectomy sheath.

11. The thrombectomy system of claim 1, further comprising the snare having a loop, the snare configured to fit within the lumen of the thrombectomy sheath and to engage a thrombus within the vein using the loop.

12. The thrombectomy system of claim 1, wherein when the thrombectomy sheath is at least partially positioned within the vein proximal to the thrombus, the balloon catheter can be positioned through the lumen of the thrombectomy sheath so that a balloon of the balloon catheter is positioned distal to the thrombus, and whereby inflation of the balloon and retraction of the balloon catheter through the thrombectomy sheath removes the thrombus from the vein.

13. The thrombectomy system of claim 5, wherein when a guidewire is positioned within the vein and when the second obturator is positioned within the lumen of the thrombectomy sheath, advancement of the second obturator and the thrombectomy sheath within the vein along the guidewire causes the vein to dilate.

14. A thrombectomy system, comprising:
a thrombectomy sheath, comprising:
a circumferential outer wall comprising a flexible polymer material reinforced with a reinforcement comprising a metallic material, configured as an elongated tube having a lumen therethrough; and
a sonovisible element positioned at or near a distal end of the circumferential outer wall;
wherein the thrombectomy sheath is sized and shaped to be at least partially positioned within a vein proximal to a thrombus or other item within the vein and further configured to expand to contact the vein to secure the thrombectomy sheath within the vein; and
wherein the lumen is sized and shaped to receive a device selected from the group consisting of a balloon catheter and a snare having a loop; and
an obturator comprising an elongated portion and a cylindrical portion at a distal end of the obturator having a larger diameter than the elongated portion, the cylindrical portion comprising a longitudinal groove defined therein configured to be self-closing.

15. The thrombectomy system of claim 14, further comprising:
a second obturator configured to fit within the lumen of the thrombectomy sheath, the second obturator comprising a flange configured to engage a proximal coupler of the thrombectomy sheath and defining a tapered portion at a distal end, the tapered portion configured to extend from the distal end of the thrombectomy sheath so to dilate the vein when advanced therein.

16. The thrombectomy system of claim 14, further comprising:
an ancillary dilator comprising an elongated portion and an ovular portion larger than the elongated portion of the ancillary dilator and having a pointed tip and defining a groove therein configured to receive at least part of a balloon catheter therein, and further comprising a fitting ring configured to fit upon the relatively larger ovular portion and rotate thereon so to lock at least part of the balloon catheter within the groove.

17. A thrombectomy method, comprising the steps of:
positioning a distal end of a thrombectomy sheath over a guidewire positioned within a vein, the thrombectomy sheath comprising:
a circumferential outer wall reinforced with a reinforcement, configured as an elongated tube having a lumen therethrough, and
a sonovisible element positioned at or near the distal end of the circumferential outer wall,
wherein the thrombectomy sheath is sized and shaped to be at least partially positioned within a vein proximal to a thrombus or other item within the vein and further configured to expand to contact the vein to secure the thrombectomy sheath within the vein, and
wherein the lumen is sized and shaped to receive a device selected from the group consisting of a balloon catheter and a snare having a loop;
advancing the thrombectomy sheath having an obturator positioned therein along the guidewire so to dilate the vein at the thrombectomy sheath, the obturator comprising an elongated portion and a cylindrical portion at a distal end of the obturator having a larger diameter than the elongated portion, the cylindrical portion comprising a longitudinal groove defined therein configured to be self-closing;
advancing the device through the lumen of the thrombectomy sheath so that a distal element of the device is positioned distal to the thrombus.

18. The thrombectomy method of claim 17, wherein the device comprises the balloon catheter, and wherein the step of advancing the device is performed to advance the balloon catheter through the lumen of the thrombectomy sheath so that a balloon of the balloon catheter is positioned distal to the thrombus; and
wherein the method further comprises the steps of:
inflating the balloon within the vein distal to the thrombus; and
retracting the balloon catheter through the thrombectomy sheath to remove the thrombus from the vein.

19. The thrombectomy method of claim 17, wherein the device comprises the snare having the loop, and wherein the step of advancing the device is performed to advance the snare having the loop through the lumen of the thrombectomy sheath so that the loop of the snare is positioned distal to the thrombus; and
wherein the method further comprises the step of:
retracting the snare through the thrombectomy sheath to remove the thrombus from the vein.

20. The thrombectomy method of claim 17, further comprising the step of:
positioning a filter distal to the thrombus within the vein, the filter configured to filter blood within the vein.

* * * * *